United States Patent
Choi et al.

(10) Patent No.: US 10,141,534 B2
(45) Date of Patent: Nov. 27, 2018

(54) COMPOUND, AND LIGHT-EMITTING DEVICE AND ELECTRONIC DEVICE INCLUDING SAME

(71) Applicant: LMS Co., Ltd., Gyeonggi-do (KR)

(72) Inventors: Jeong Og Choi, Seoul (KR); Joon Ho Jung, Gyeonggi-do (KR); Oh Kwan Kwon, Gyeonggi-do (KR)

(73) Assignee: LMS CO.,LTD., Gyeonggi-do (KR)

( * ) Notice: Subject to any disclaimer, the term of this patent is extended or adjusted under 35 U.S.C. 154(b) by 468 days.

(21) Appl. No.: 14/783,001

(22) PCT Filed: Apr. 7, 2014

(86) PCT No.: PCT/KR2014/002974
§ 371 (c)(1),
(2) Date: Oct. 7, 2015

(87) PCT Pub. No.: WO2014/168386
PCT Pub. Date: Oct. 16, 2014

(65) Prior Publication Data
US 2016/0056402 A1    Feb. 25, 2016

(30) Foreign Application Priority Data
Apr. 8, 2013    (KR) .......... 10-2013-0038223

(51) Int. Cl.
*H01L 51/50* (2006.01)
*C07D 333/76* (2006.01)
(Continued)

(52) U.S. Cl.
CPC .......... *H01L 51/5072* (2013.01); *C07C 15/28* (2013.01); *C07C 43/20* (2013.01);
(Continued)

(58) Field of Classification Search
CPC ..... C07C 15/28; C07C 2603/24; C07C 43/20; C07D 213/06; C07D 213/16;
(Continued)

(56) References Cited

U.S. PATENT DOCUMENTS 6,361,886 B2 *   3/2002   Shi ........................ H01L 51/005
                                                              252/301.16
6,582,837 B1 *   6/2003   Toguchi .............. H01L 51/0058
                                                              313/504
(Continued)

FOREIGN PATENT DOCUMENTS

EP        1385221 A2      1/2004
JP    2005-314239 A  *  11/2005
(Continued)

OTHER PUBLICATIONS

Machine translation for JP 2012-067077 A (publication date: Apr. 2012).*

*Primary Examiner* — Dawn L Garrett
(74) *Attorney, Agent, or Firm* — Polsinelli PC

(57) ABSTRACT

A novel compound according to the present invention may improve the capability of transporting electrons to a light-emitting layer in a light-emitting device, and may improve the light-emitting efficiency and increase the lifespan of the light-emitting device by using the compound.

13 Claims, 2 Drawing Sheets

(51) Int. Cl.
*C07C 15/28* (2006.01)
*C07D 213/16* (2006.01)
*H01L 51/00* (2006.01)
*C09K 11/06* (2006.01)
*C07D 235/06* (2006.01)
*C07D 213/06* (2006.01)
*C07D 213/30* (2006.01)
*C07C 43/20* (2006.01)

(52) U.S. Cl.
CPC ......... *C07D 213/06* (2013.01); *C07D 213/16* (2013.01); *C07D 213/30* (2013.01); *C07D 235/06* (2013.01); *C07D 333/76* (2013.01); *C09K 11/06* (2013.01); *H01L 51/0052* (2013.01); *H01L 51/0058* (2013.01); *H01L 51/0062* (2013.01); *H01L 51/0067* (2013.01); *H01L 51/0074* (2013.01); *C07C 2603/24* (2017.05)

(58) Field of Classification Search
CPC .. C07D 213/30; C07D 235/06; C07D 333/76; H01L 51/0052; H01L 51/0058; H01L 51/0062; H01L 51/0067; H01L 51/0074; H01L 51/5072
See application file for complete search history.

(56) References Cited

U.S. PATENT DOCUMENTS

| | | | | |
|---|---|---|---|---|
| 2004/0018380 | A1* | 1/2004 | Aziz | C07D 219/06 428/690 |
| 2007/0060777 | A1* | 3/2007 | Moriwaki | C07C 7/173 570/226 |
| 2007/0247063 | A1* | 10/2007 | Murase | C07D 209/86 313/504 |
| 2010/0295444 | A1* | 11/2010 | Kuma | H01L 51/5004 313/504 |
| 2013/0001526 | A1* | 1/2013 | Kwak | H01L 51/5265 257/40 |

FOREIGN PATENT DOCUMENTS

| | | |
|---|---|---|
| JP | 4807013 | 8/2011 |
| JP | 201267077 A | 4/2012 |
| JP | 2013-145886 A * | 7/2013 |
| KR | 10-20060134979 A | 12/2006 |
| KR | 10-20080046657 A | 5/2008 |
| KR | 10-20120041110 | 4/2012 |
| WO | WO 2010/134350 A1 | 11/2010 |

* cited by examiner

[Fig.1]
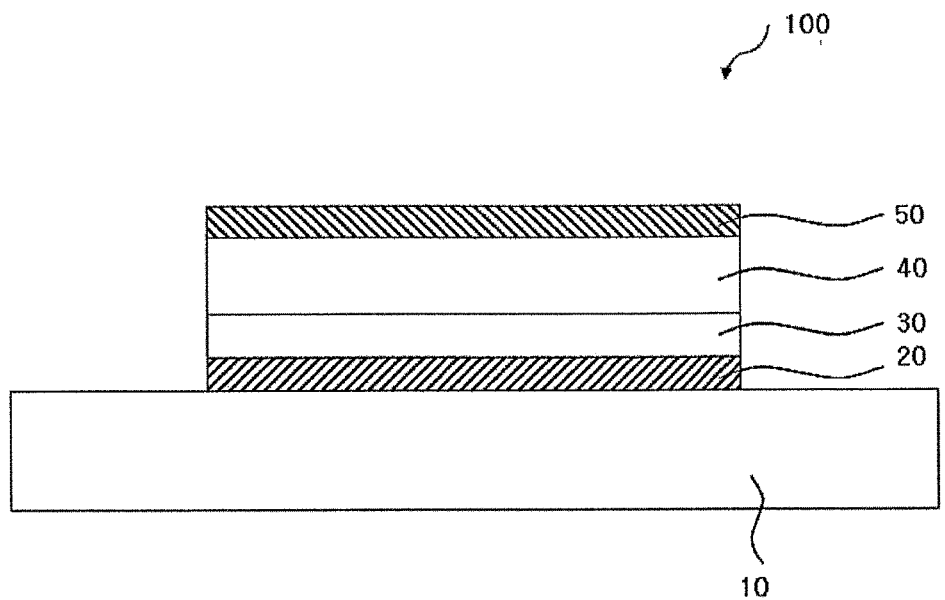
[Fig.2]
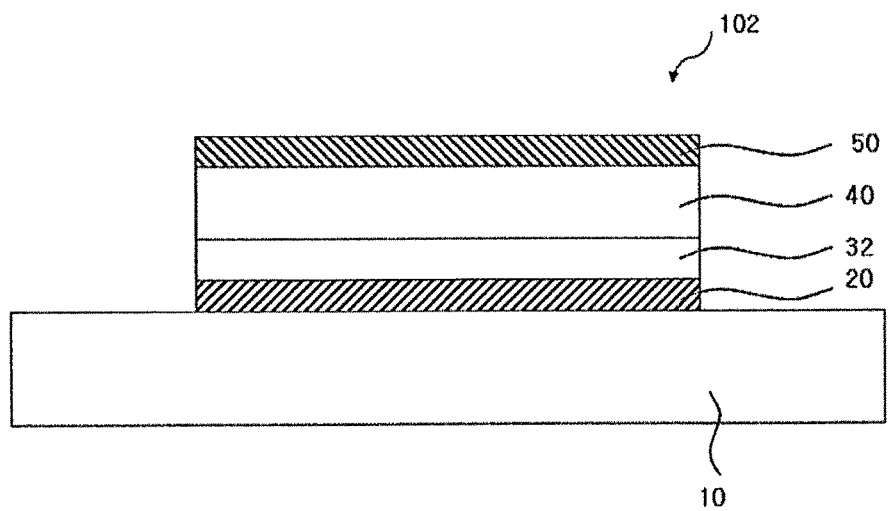

[Fig.3]
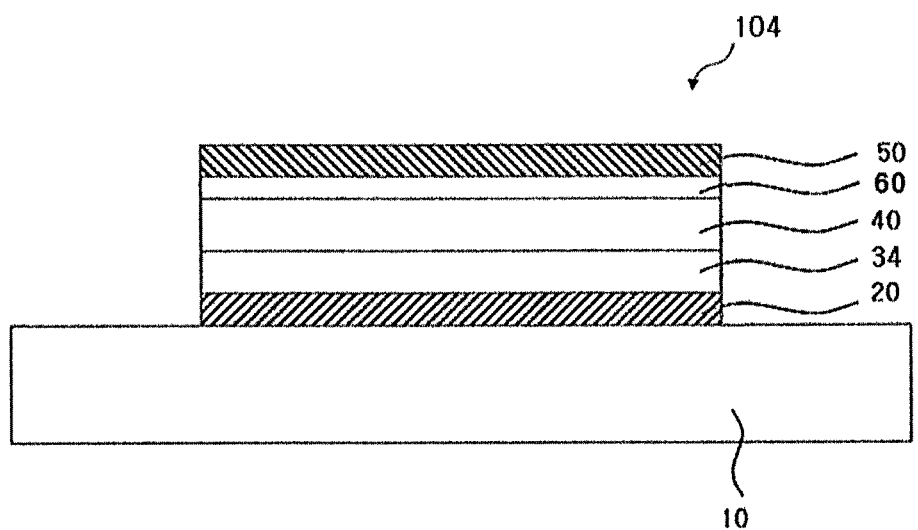

COMPOUND, AND LIGHT-EMITTING DEVICE AND ELECTRONIC DEVICE INCLUDING SAME

This application is the United States national phase of International Application No. PCT/KR2014/002974 filed Apr. 7, 2014, and claims priority to Korean Patent Application No. 10-2013-0038223 filed Apr. 8, 2013, the disclosures of which are hereby incorporated by reference.

BACKGROUND

Field of the Invention

The present invention relates to a novel compound, and a light-emitting device and an electronic device including the same, and more particularly, to a compound for an organic light-emitting device, and a light-emitting device and an electronic device including the same.

Background Art

In general, a light-emitting device includes two electrodes facing each other and a light-emitting layer including a light-emitting compound interposed between the electrodes. When current flows between the electrodes, the light-emitting compound produces light. A display device using the light-emitting device does not need a separate light source device, and thus may decrease the weight, size or thickness of the display device. Further, the display device using the light-emitting device has advantages in that the viewing angle, the contrast ratio, the color reproducibility, and the like are excellent and power consumption is low as compared to a display device using a backlight and a liquid crystal.

The materials used as an organic material layer of an organic light-emitting device among the light-emitting devices may be classified into a light-emitting material, a hole injection material, a hole transport material, an electron transport material, an electron injection material, and the like according to the function. The light-emitting materials may be divided into a polymer-type and a low molecular weight-type according to the molecular weight, and may be divided into blue, green, and red light-emitting materials, and the like according to the light-emitting color.

When a single material is used as a light-emitting material, there may occur a problem in that the maximum light-emitting wavelength is moved into the long wavelength by the interaction between molecules, the color purity is reduced, or efficiency of the device is lowered by the light-emitting reducing effect. In order to complement the problem, a light-emitting layer composed of a host/dopant system may be applied to the light-emitting device. An exciton formed in the light-emitting layer is transferred to a dopant by using a host material, which is a main material forming the light-emitting layer, and a small amount of the dopant having an energy band gap lower than that of the host material, so that the light-emitting device may efficiently emit light.

However, the light-emitting device still has problems in that the lifespan of light emission is short and the power efficiency is low. In order to solve these problems, various compounds have been developed as a material for the light-emitting device, but there is a limitation in manufacturing a light-emitting device which satisfies both the lifespan of light emission and the power efficiency.

PRIOR ART DOCUMENT

Patent Document

Japanese Patent No. 4807013
Japanese Patent Application Laid-Open No. 2012-067077
Korean Patent Application Laid-Open No. 2006-0134979

SUMMARY OF THE INVENTION

Technical Problem

Thus, a technical problem of the present invention has been contrived in view of these circumstances, and an object of the present invention is to provide a novel compound which may improve the light emission efficiency and increase the lifespan in a light-emitting device.

Another object of the present invention is to provide a light-emitting device including the compound.

Still another object of the present invention is to provide an electronic device including the light-emitting device.

Technical Solution

A compound according to an exemplary embodiment for realizing the object of the present invention is represented by the following Formula 1.

A compound represented by the following Formula 1:

[Formula 1]

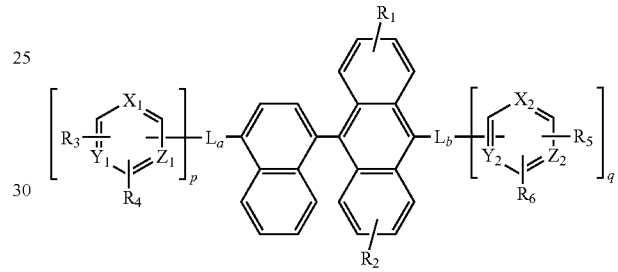

In Formula 1, $L_a$ and $L_b$ each independently represent *-$L_1$-$L_2$-$L_3$-*, and $L_1$, $L_2$, and $L_3$ each independently represent a single bond, or a phenylene group which is unsubstituted or substituted with an aryl group having 1 to 12 carbon atoms, $R_1$ and $R_2$ each independently represent hydrogen, an alkyl group having 1 to 30 carbon atoms, or an alkoxy group having 1 to 30 carbon atoms, $X_1$, $X_2$, $Y_1$, $Y_2$, $Z_1$, and $Z_2$ each independently represent C—$R_a$ or N, p and q each independently represent 0 or 1, in which p+q=1 or 2, $R_a$, $R_3$, $R_4$, $R_5$, and $R_6$ each independently represent hydrogen, a phenyl group, a pyridinyl group, or the following Formula 2,

[Formula 2]

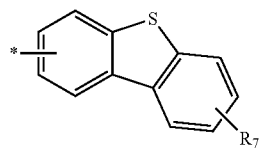

when at least one of $R_3$ and $R_4$ is a substituent represented by Formula 2, at least one of $R_5$ and $R_6$ is a substituent represented by Formula 2, and $R_7$ represents hydrogen or an alkyl group having 1 to 30 carbon atoms.

A light-emitting device for realizing another object of the present invention is provided. The light-emitting device includes a first electrode, a second electrode, and a light-emitting layer, in which the light-emitting layer is disposed between the first and second electrodes.

In one exemplary embodiment, the light-emitting layer includes the compound represented by Formula 1.

In another exemplary embodiment, the light-emitting device further includes an electron transporting layer disposed between the light-emitting layer and the second electrode, and the electron transporting layer includes the compound represented by Formula 1.

Effect of the Invention

According to the novel compound, and the light-emitting device and the electronic device including the same, the novel compound of the present invention may improve the capability of transporting electrons from the light-emitting device to a light-emitting layer.

Further, it is possible improve the light-emitting efficiency and increase the lifespan of the light-emitting device by using the compound.

BRIEF DESCRIPTION OF DRAWINGS

FIG. 1 is a cross-sectional view for describing a light-emitting device according to an exemplary embodiment of the present invention.

FIG. 2 is a cross-sectional view for describing a light-emitting device according to another exemplary embodiment of the present invention.

FIG. 3 is a cross-sectional view for describing a light-emitting device according to still another exemplary embodiment of the present invention.

DETAILED DESCRIPTION OF THE INVENTION

Hereinafter, a novel compound according to the present invention will be first described, and a light-emitting device including the compound will be described in more detail with reference to the accompanying drawings.

The compound according to the present invention is represented by the following Formula 1.

[Formula 1]

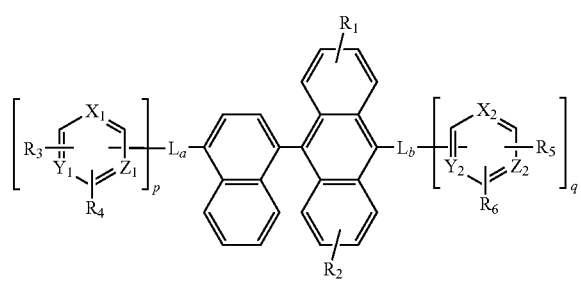

In Formula 1, $L_a$ and $L_b$ each independently represent $*-L_1-L_2-L_3-*$, and $L_1$, $L_2$, and $L_3$ each independently represent a single bond, or a phenylene group which is unsubstituted or substituted with an aryl group having 1 to 12 carbon atoms, $R_1$ and $R_2$ each independently represent hydrogen, an alkyl group having 1 to 30 carbon atoms, or an alkoxy group having 1 to 30 carbon atoms, $X_1$, $X_2$, $Y_1$, $Y_2$, $Z_1$, and $Z_2$ each independently represent $C-R_a$ or N, p and q each independently represent 0 or 1, in which p+q=1 or 2, $R_a$, $R_3$, $R_4$, $R_5$, and $R_6$ each independently represent hydrogen, a phenyl group, a pyridinyl group, or the following Formula 2,

[Formula 2]

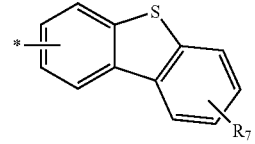

when at least one of $R_3$ and $R_4$ is the substituent represented by Formula 2, at least one of $R_5$ and $R_6$ is the substituent represented by Formula 2, and $R_7$ represents hydrogen or an alkyl group having 1 to 30 carbon atoms.

In Formula 1, specific examples of "the aryl group" include a phenyl group or a biphenyl group.

In the present invention, "an alkyl group" is defined as a functional group derived from a linear or branched, saturated hydrocarbon.

Specific examples of the alkyl group include a methyl group, an ethyl group, an n-propyl group, an iso-propyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

In an exemplary embodiment, the compound represented by Formula 1 may include a compound represented by the following Formula 3.

[Formula 3]

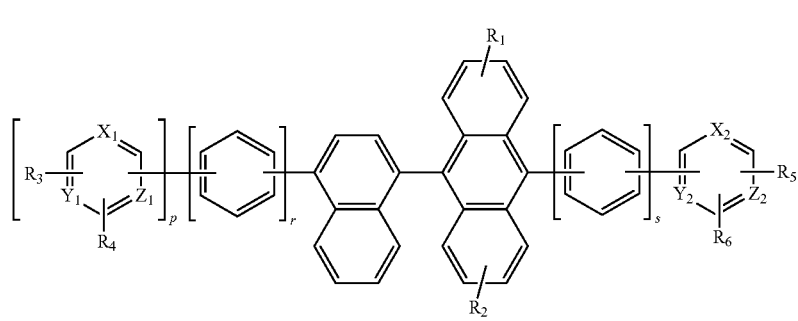

In Formula 3,

R$_1$ and R$_2$ each independently represent hydrogen, an alkyl group having 1 to 30 carbon atoms, or an alkoxy group having 1 to 30 carbon atoms, X$_1$, X$_2$, Y$_1$, Y$_2$, Z$_1$, and Z$_2$ each independently represent C—R$_a$ or N, in which at least one of X$_1$, Y$_1$, and Z$_1$ and at least one of X$_2$, Y$_2$, and Z$_2$ represent N, p, r, and s each independently represent 0 or 1, and R$_a$, R$_3$, R$_4$, R$_5$, and R$_6$ each independently represent hydrogen or a phenyl group.

The compound represented by Formula 3 according to the present invention may be selected from the compounds represented by Structures 1 to 9 of the following Table 1.

TABLE 1

| No. | Structure |
|---|---|
| 1 | 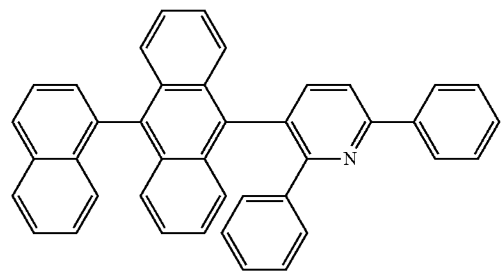 [SMILES: c1ccc(-c2ccc(-c3c4ccccc4c(-c4cccc5ccccc45)c4ccccc34)c(-c3ccccc3)n2)cc1] |
| 2 | 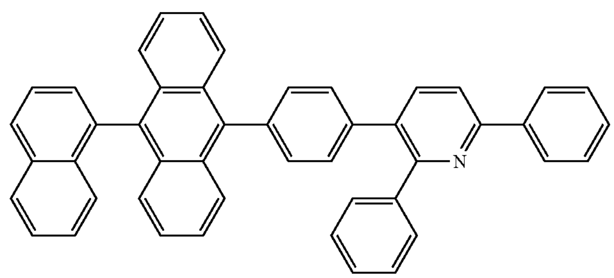 [SMILES: c1ccc(-c2ccc(-c3ccc(-c4c5ccccc5c(-c5cccc6ccccc56)c5ccccc45)cc3)c(-c3ccccc3)n2)cc1] |
| 3 | 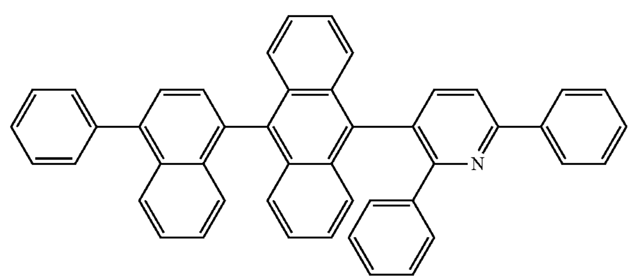 [SMILES: c1ccc(-c2ccc(-c3c4ccccc4c(-c4ccc(-c5ccccc5)c5ccccc45)c4ccccc34)c(-c3ccccc3)n2)cc1] |
| 4 | 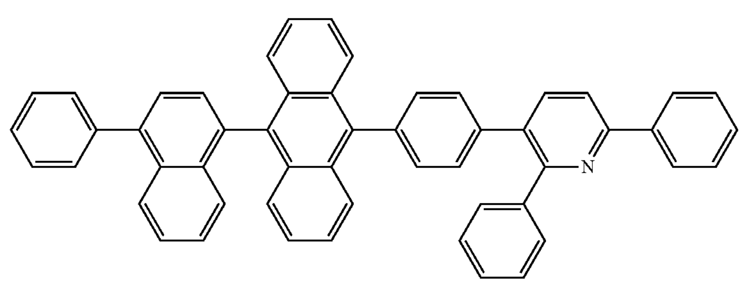 [SMILES: c1ccc(-c2ccc(-c3ccc(-c4c5ccccc5c(-c5ccc(-c6ccccc6)c6ccccc56)c5ccccc45)cc3)c(-c3ccccc3)n2)cc1] |
| 5 | 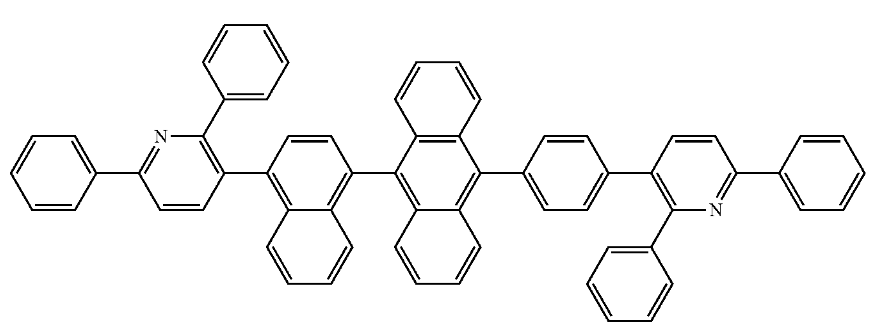 [SMILES: c1ccc(-c2ccc(-c3ccc(-c4c5ccccc5c(-c5ccc(-c6ccc(-c7ccccc7)nc6-c6ccccc6)c6ccccc56)c5ccccc45)cc3)c(-c3ccccc3)n2)cc1] |

TABLE 1-continued

| No. | Structure |
|---|---|
| 6 | 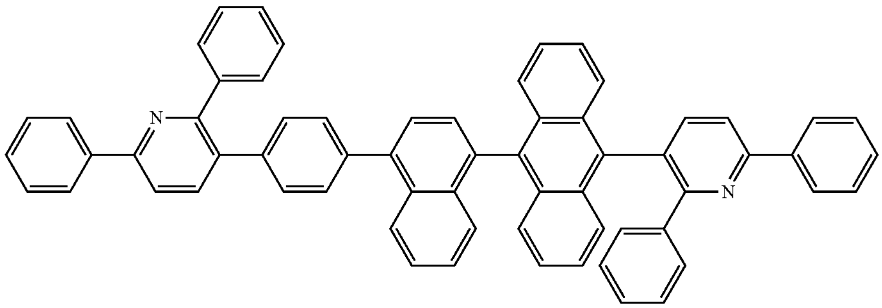 [SMILES: c1ccc(-c2ccc(-c3ccc(-c4ccc(-c5c6ccccc6c(-c6ccc(-c7ccccc7)nc6-c6ccccc6)c6ccccc56)c5ccccc45)cc3)c(-c3ccccc3)n2)cc1] |
| 7 | 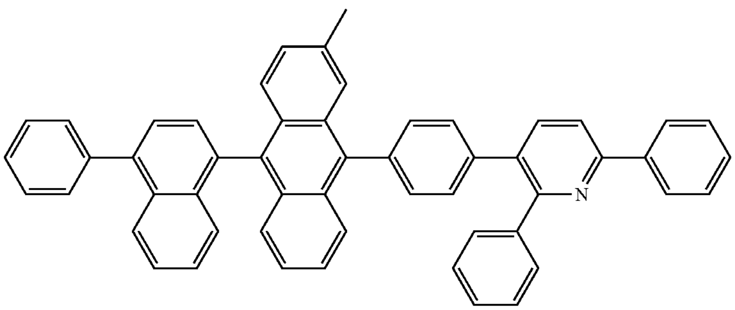 [SMILES: Cc1ccc2c(-c3ccc(-c4ccccc4)c4ccccc34)c3ccccc3c(-c3ccc(-c4ccc(-c5ccccc5)nc4-c4ccccc4)cc3)c2c1] |
| 8 | 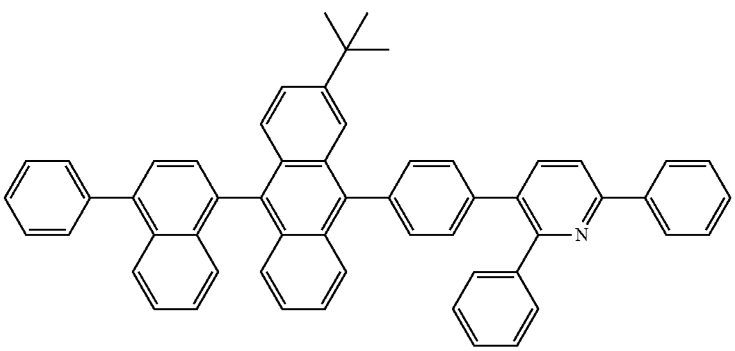 [SMILES: CC(C)(C)c1ccc2c(-c3ccc(-c4ccccc4)c4ccccc34)c3ccccc3c(-c3ccc(-c4ccc(-c5ccccc5)nc4-c4ccccc4)cc3)c2c1] |
| 9 | 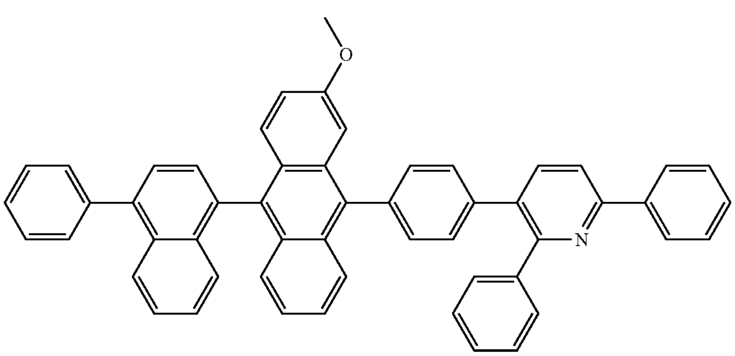 [SMILES: COc1ccc2c(-c3ccc(-c4ccccc4)c4ccccc34)c3ccccc3c(-c3ccc(-c4ccc(-c5ccccc5)nc4-c4ccccc4)cc3)c2c1] |

In an exemplary embodiment, the compound represented by Formula 3 may include a compound represented by the following Formula 3-1.

[Formula 3-1]

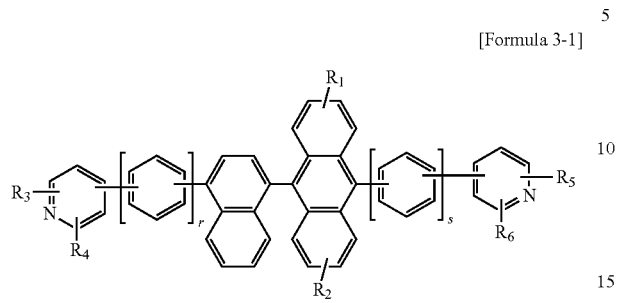

In Formula 3-1, $R_1$ and $R_2$ each independently represent hydrogen, an alkyl group having 1 to 30 carbon atoms, or an alkoxy group having 1 to 30 carbon atoms, r and s each identically represent 0 or 1, and $R_3$, $R_4$, $R_5$, and $R_6$ represent a phenyl group.

The compound represented by Formula 3-1 according to the present invention may be represented by Structure 1 or 2 of the following Table 2.

TABLE 2

| No. | Structure |
|---|---|
| 1 | 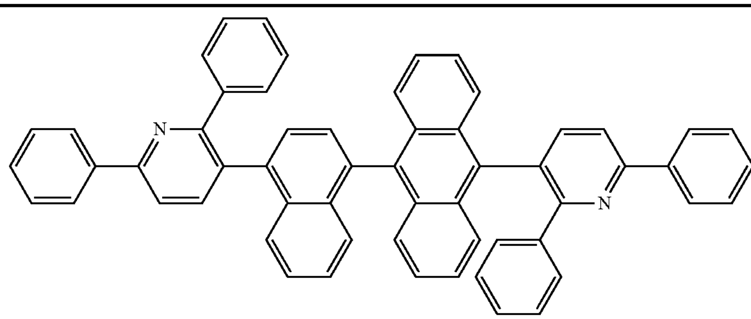 |
| 2 | 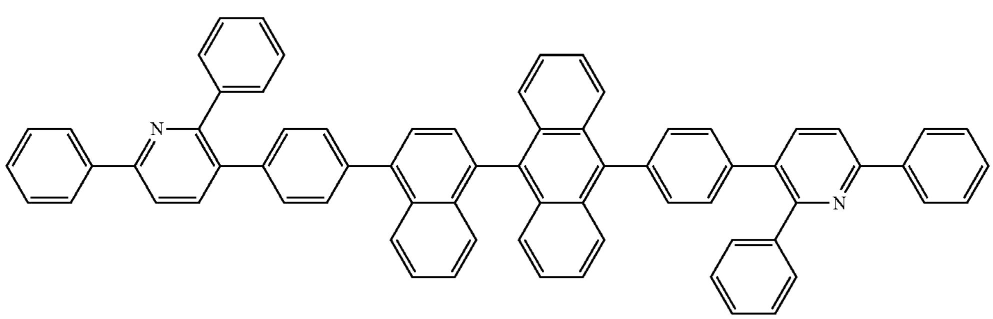 [SMILES: c1ccc(-c2ccc(-c3ccc(-c4ccc(-c5c6ccccc6c(-c6ccc(-c7ccc(-c8ccccc8)nc7-c7ccccc7)cc6)c6ccccc56)c5ccccc45)cc3)c(-c3ccccc3)n2)cc1] |

In an exemplary embodiment, the compound represented by Formula 1 may include a compound represented by the following Formula 4.

[Formula 4]

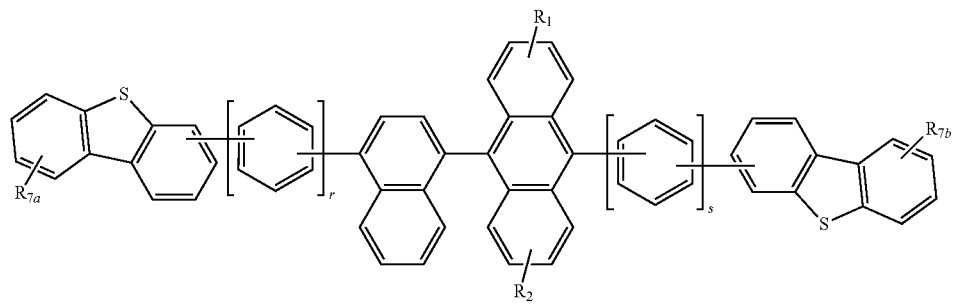

In Formula 4, $R_1$ and $R_2$ each independently represent hydrogen, an alkyl group having 1 to 30 carbon atoms, or an alkoxy group having 1 to 30 carbon atoms, r and s each independently represent 0 or 1, and $R_{7a}$ and $R_{7b}$ each independently represent hydrogen, or an alkyl group having 1 to 30 carbon atoms.

The compound represented by Formula 4 according to the present invention may be selected from the compounds represented by Structures 1 to 10 of the following Table 3.

TABLE 3

| No. | Structure |
|---|---|
| 1 | 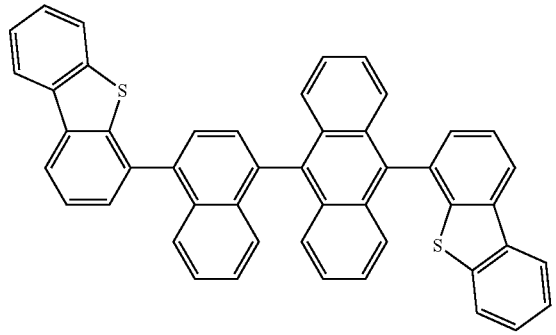 [SMILES: c1ccc2c(c1)sc1c(-c3ccc(-c4c5ccccc5c(-c5cccc6c5sc5ccccc56)c5ccccc45)c4ccccc34)cccc12] |
| 2 | 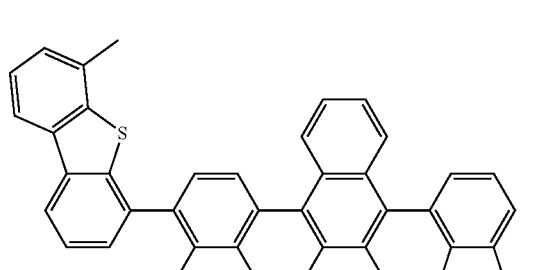 |

TABLE 3-continued
| No. | Structure |
|---|---|
| 3 | 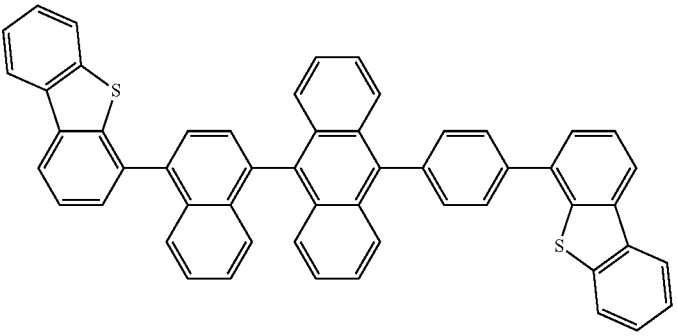 [SMILES: c1ccc2c(c1)sc1c(-c3ccc(-c4c5ccccc5c(-c5ccc(-c6cccc7c6sc6ccccc67)c6ccccc56)c5ccccc45)cc3)cccc12] |
| 4 | 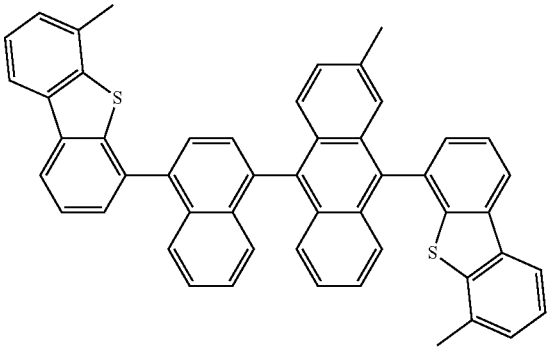 [SMILES: Cc1ccc2c(-c3ccc(-c4cccc5c4sc4c(C)cccc45)c4ccccc34)c3ccccc3c(-c3cccc4c3sc3c(C)cccc34)c2c1] |
| 5 | 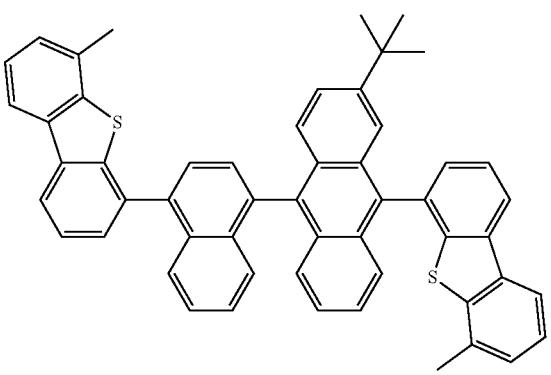 [SMILES: Cc1cccc2c1sc1c(-c3ccc(-c4c5ccccc5c(-c5cccc6c5sc5c(C)cccc56)c5cc(C(C)(C)C)ccc45)c4ccccc34)cccc12] |
| 6 | 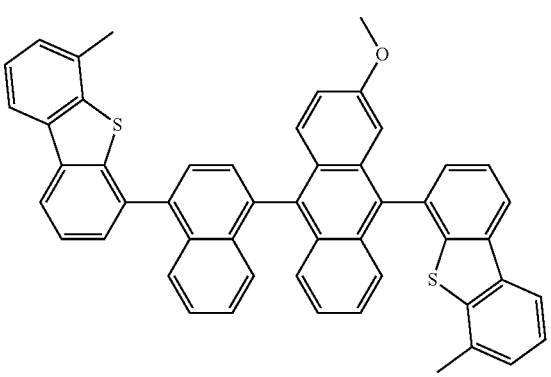 [SMILES: COc1ccc2c(-c3ccc(-c4cccc5c4sc4c(C)cccc45)c4ccccc34)c3ccccc3c(-c3cccc4c3sc3c(C)cccc34)c2c1] |

TABLE 3-continued
| No. | Structure |
|---|---|
| 7 | 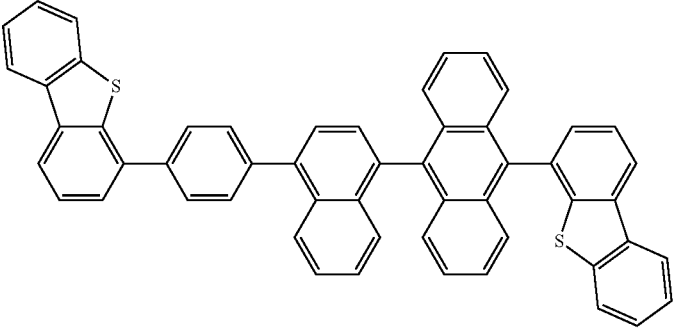 [SMILES: c1ccc2c(c1)sc1c(-c3ccc(-c4ccc(-c5c6ccccc6c(-c6cccc7c6sc6ccccc67)c6ccccc56)c5ccccc45)cc3)cccc12] |
| 8 | 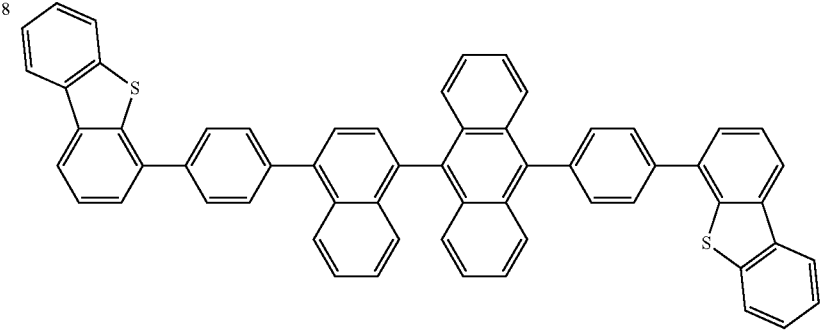 |
| 9 | 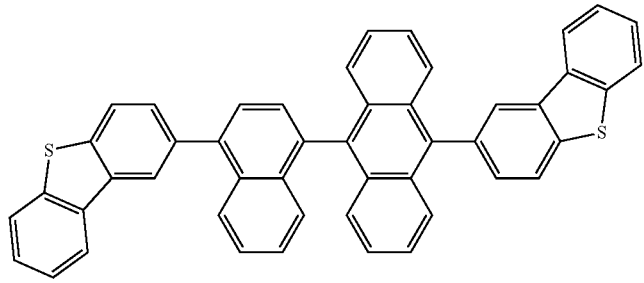 [SMILES: c1ccc2c(c1)sc1ccc(-c3ccc(-c4c5ccccc5c(-c5ccc6sc7ccccc7c6c5)c5ccccc45)c4ccccc34)cc12] |
| 10 | 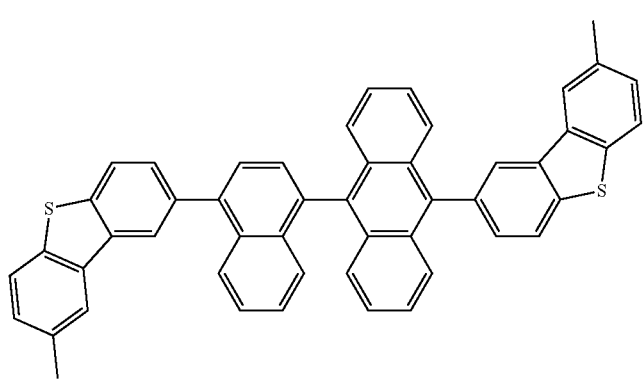 [SMILES: Cc1ccc2sc3ccc(-c4ccc(-c5c6ccccc6c(-c6ccc7sc8ccc(C)cc8c7c6)c6ccccc56)c5ccccc45)cc3c2c1] |
In an exemplary embodiment, the compound represented by Formula 1 may include a compound represented by the following Formula 5.

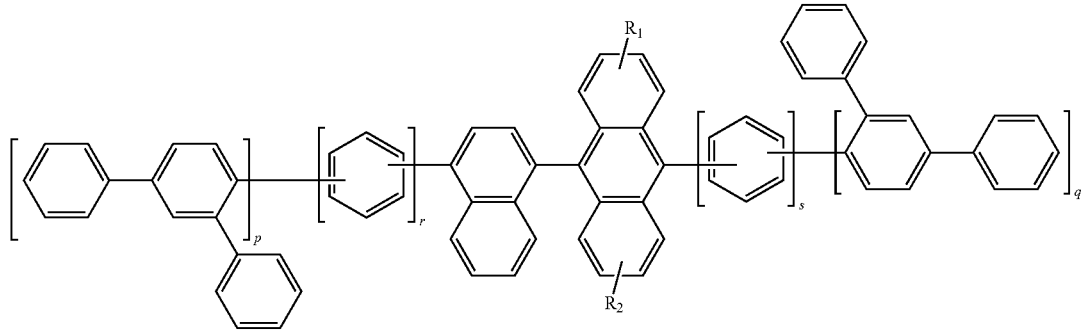

[Formula 5]

In Formula 5, $R_1$ and $R_2$ each independently represent hydrogen, an alkyl group having 1 to 30 carbon atoms, or an alkoxy group having 1 to 30 carbon atoms, p and q each independently represent 0 or 1, in which p+q=1 or 2, and r and s each independently represent an integer of 0 to 2.

The compound represented by Formula 5 according to the present invention may be selected from the compounds represented by Structures 1 to 9 of the following Table 4.

TABLE 4

| No. | Structure |
|---|---|
| 1 | 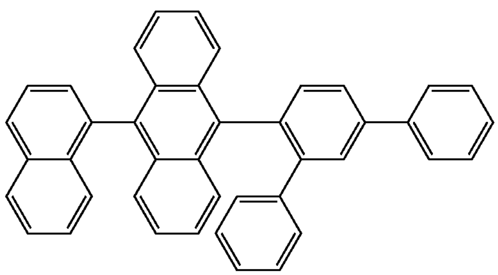 [SMILES: c1ccc(-c2ccc(-c3c4ccccc4c(-c4cccc5ccccc45)c4ccccc34)c(-c3ccccc3)c2)cc1] |
| 2 | 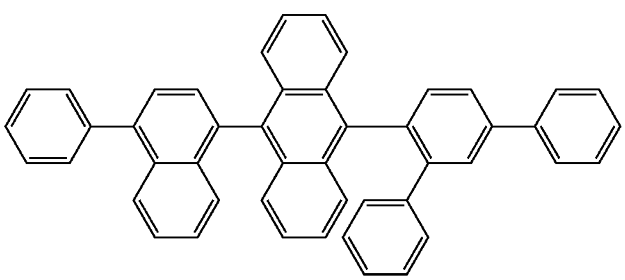 [SMILES: c1ccc(-c2ccc(-c3c4ccccc4c(-c4ccc(-c5ccccc5)c5ccccc45)c4ccccc34)c(-c3ccccc3)c2)cc1] |
| 3 | 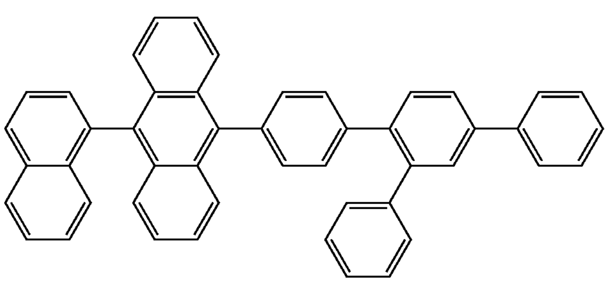 [SMILES: c1ccc(-c2ccc(-c3ccc(-c4c5ccccc5c(-c5cccc6ccccc56)c5ccccc45)cc3)c(-c3ccccc3)c2)cc1] |

TABLE 4-continued
| No. | Structure |
|---|---|
| 4 | 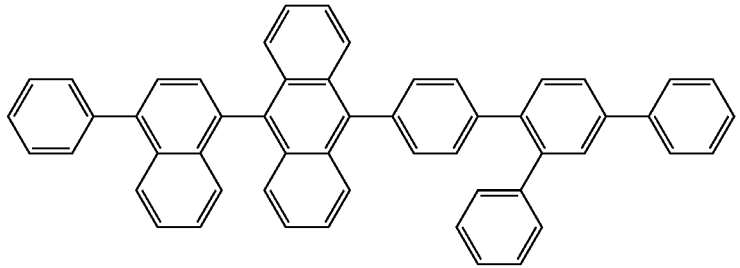 [SMILES: c1ccc(-c2ccc(-c3ccc(-c4c5ccccc5c(-c5ccc(-c6ccccc6)c6ccccc56)c5ccccc45)cc3)c(-c3ccccc3)c2)cc1] |
| 5 | 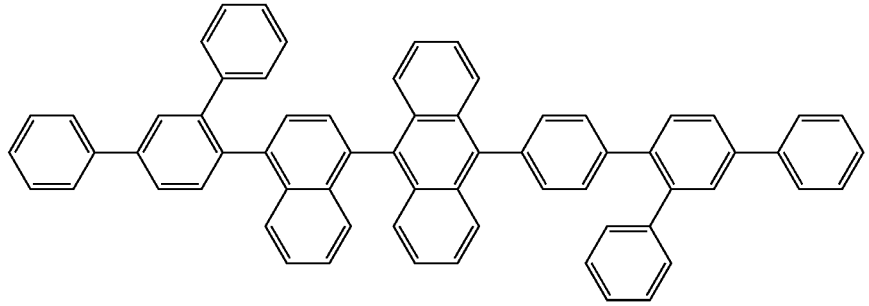 [SMILES: c1ccc(-c2ccc(-c3ccc(-c4c5ccccc5c(-c5ccc(-c6ccc(-c7ccccc7)cc6-c6ccccc6)c6ccccc56)c5ccccc45)cc3)c(-c3ccccc3)c2)cc1] |
| 6 | 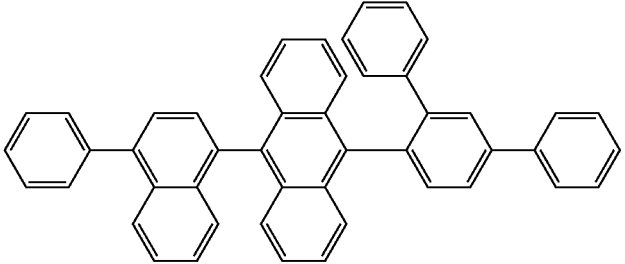 [SMILES: c1ccc(-c2ccc(-c3c4ccccc4c(-c4ccc(-c5ccccc5)c5ccccc45)c4ccccc34)c(-c3ccccc3)c2)cc1] |
| 7 | 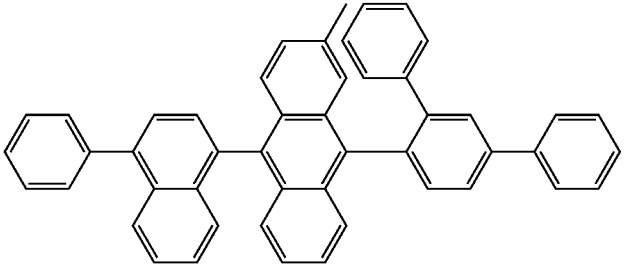 [SMILES: Cc1ccc2c(-c3ccc(-c4ccccc4)c4ccccc34)c3ccccc3c(-c3ccc(-c4ccccc4)cc3-c3ccccc3)c2c1] |
| 8 | 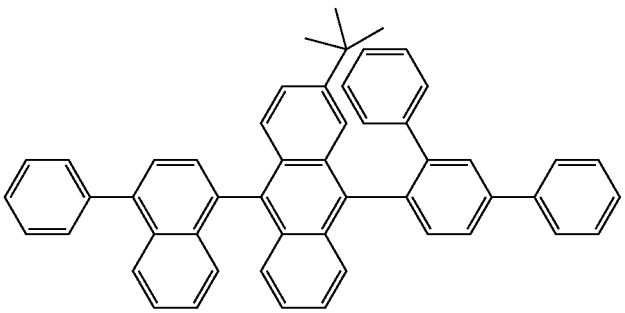 [SMILES: CC(C)(C)c1ccc2c(-c3ccc(-c4ccccc4)c4ccccc34)c3ccccc3c(-c3ccc(-c4ccccc4)cc3-c3ccccc3)c2c1] |

TABLE 4-continued

| No. | Structure |
|---|---|
| 9 | 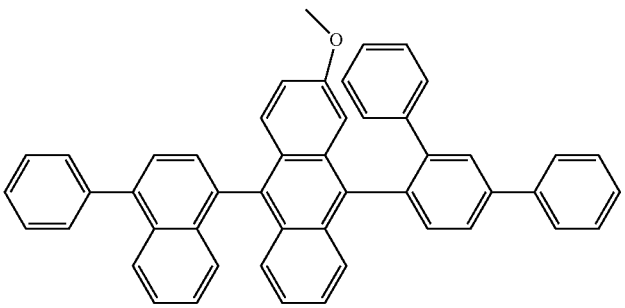 [SMILES: COc1ccc2c(-c3ccc(-c4ccccc4)c4ccccc34)c3ccccc3c(-c3ccc(-c4ccccc4)cc3-c3ccccc3)c2c1] |

In an exemplary embodiment, the compound represented by Formula 5 may include a compound represented by the following Formula 5-1.

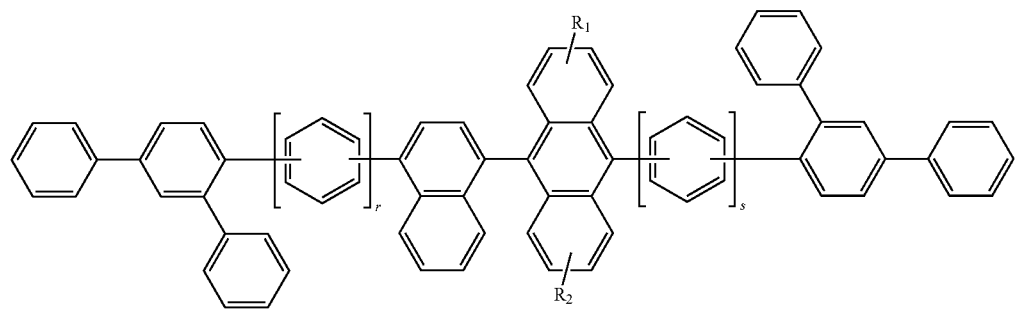

[Formula 5-1]

In Formula 5-1, $R_1$ and $R_2$ each independently represent hydrogen, an alkyl group having 1 to 30 carbon atoms, or an alkoxy group having 1 to 30 carbon atoms, and r and s each identically represent an integer of 0 to 2.

The compound represented by Formula 5-1 according to the present invention may be represented by Structures 1 and 2 of the following Table 5.

TABLE 5

| No. | Structure |
|---|---|
| 1 | 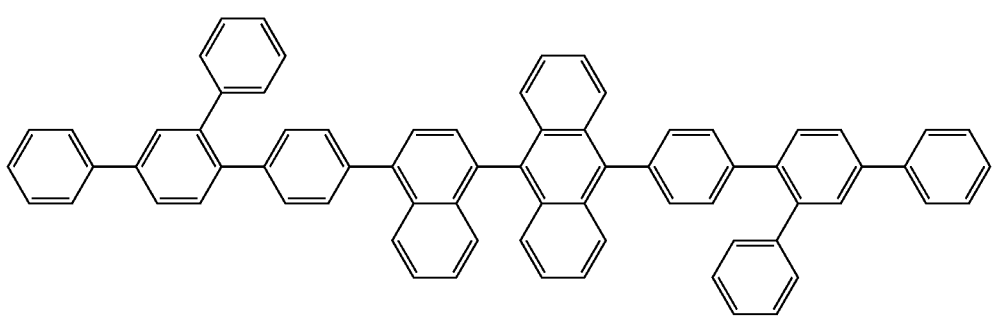 |

TABLE 5-continued

| No. | Structure |
|---|---|
| 2 | 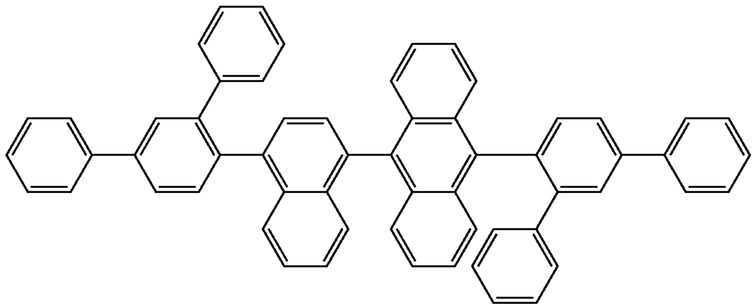 [SMILES: c1ccc(-c2ccc(-c3ccc(-c4c5ccccc5c(-c5ccc(-c6ccccc6)cc5-c5ccccc5)c5ccccc45)c4ccccc34)c(-c3ccccc3)c2)cc1] |

Hereinafter, a light-emitting device having an organic layer including the novel compound according to the present invention will be described with reference to the accompanying drawings. Hereinafter, the case where an organic layer including the novel compound according to the present invention is an electron transporting layer or a light-emitting layer will be described, but the structure of the light-emitting device including the compound is not limited by the accompanying drawings and the following description.

FIG. 1 is a cross-sectional view for describing a light-emitting device according to an exemplary embodiment of the present invention.

Referring to FIG. 1, a light-emitting device 100 includes a first electrode 20, a hole transport layer 30, a light-emitting layer 40, and a second electrode 50, which are formed on a base substrate 10. The light-emitting device 100 may be an organic light emitting diode (OLED).

The first electrode 20 may be formed of a conductive material on the base substrate 10. As an example, the first electrode 20 may be a transparent electrode. In this case, the first electrode 20 may be formed of indium tin oxide (ITO). In contrast, the first electrode 20 may be an opaque (reflective) electrode. In this case, the first electrode 20 may have an ITO/silver (Ag)/ITO structure. The first electrode 20 may become an anode of the light-emitting device 100.

The hole transport layer 30 is formed on the first electrode 20 to be interposed between the first electrode 20 and the light-emitting layer 40. The hole transport layer 30 may include a hole transporting layer and/or a hole injecting layer. As a material which forms the hole transport layer 30, various commercially available materials may be used without particular limitation.

The light-emitting layer 40 may be disposed between the hole transport layer 30 and the second electrode 50. The wavelength of light emitted by the light-emitting layer 40 may vary depending on the kind of compound which forms the light-emitting layer 40.

The light-emitting layer 40 includes at least one of the compounds represented by the following Formula 4 and the following Formula 5 as a light-emitting material.

[Formula 4]

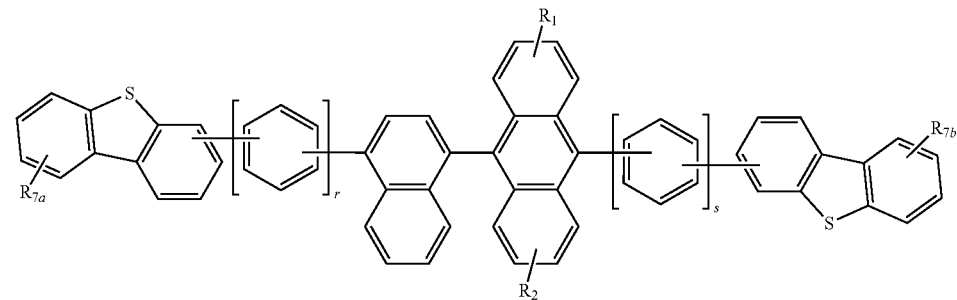

[Formula 5]

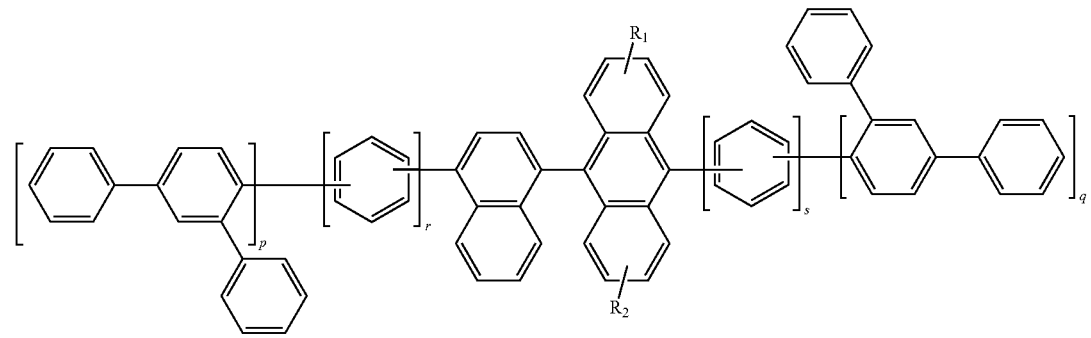

The compound represented by Formula 4 or 5 is a novel compound according to the present invention and may be substantially the same as those described above. Accordingly, the overlapping specific description of each of $R_1$, $R_2$, $R_{7a}$, $R_{7b}$, p, q, r, and s will be omitted.

In the present invention, the compound represented by Formula 4 or 5 may be used as a host compound which is a main material constituting the light-emitting layer 40. In this case, the light-emitting layer 40 may further include a light-emitting material which emits blue light together with the host compound as a dopant.

As the light-emitting material, a compound represented by the following Formula X may be used.

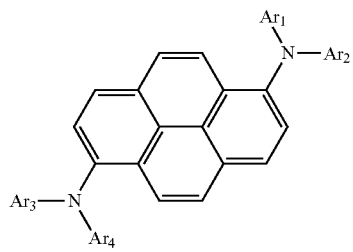

[Formula X]

In Formula X, $Ar_1$, $Ar_2$, $Ar_3$, and $Ar_4$ each independently represent an aryl group having 1 to 18 carbon atoms, and any one of the hydrogen atoms of each of $Ar_1$, $Ar_2$, $Ar_3$, and $Ar_4$ may be substituted with an alkyl group having 1 to 10 carbon atoms.

Specific examples of the compound represented by Formula X include compounds represented by the following Structure a, Structure b, or Structure c. These may be used either alone or in combination of two or more thereof.

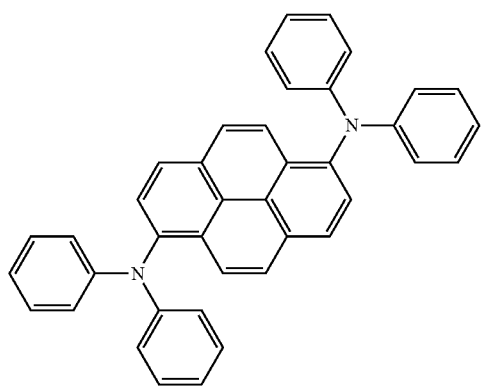

[Structure a]

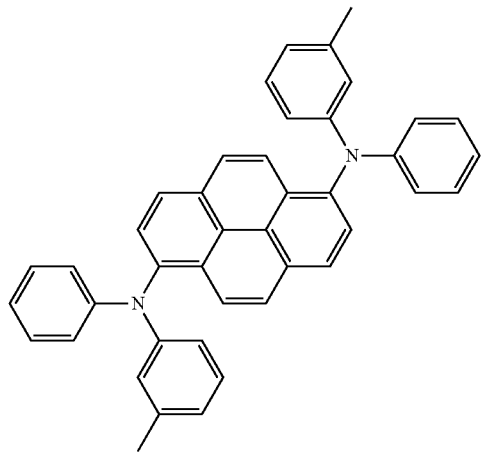

[Structure b]

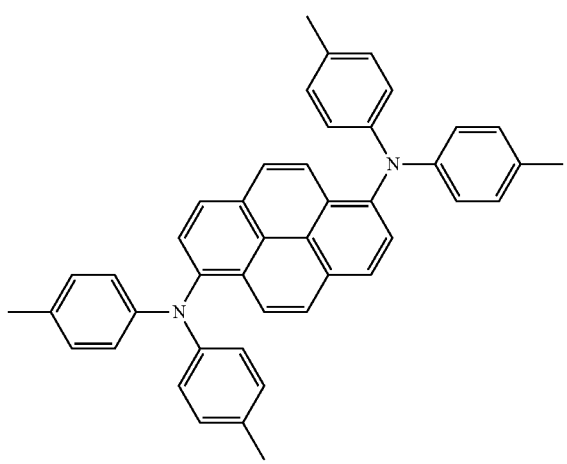

[Structure c]

The second electrode 50 may be formed of a conductive material on the light-emitting layer 40. When the first electrode 20 is a transparent electrode, the second electrode 50 may be an opaque (reflective) electrode. In this case, the second electrode 50 may be an aluminum electrode. In contrast, when the first electrode 20 is an opaque electrode, the second electrode 50 may be a transparent or semi-transparent electrode, and in this case, the second electrode 50 may have a thickness of 100 Å to 150 Å. As a material which forms the opaque transparent, an alloy including magnesium and silver may be used. The second electrode 50 may become a cathode of the light-emitting device 100.

Although not illustrated in the drawing, an electron transporting layer (ETL) and/or an electron injecting layer (EIL) may be formed as an electron transport layer between the light-emitting layer 40 and the second electrode 50. For each of the electron transporting layer or the electron injecting layer, various commercially available materials may be used without particular limitation.

When current flows between the first and second electrodes 20 and 50 of the light-emitting device 100, a hole injected from the first electrode 20 to the light-emitting layer 40 and an electron injected from the second electrode 50 to the light-emitting layer 40 combine with each other form an exciton. While the exciton is transferred to a bottom state, light having a wavelength at a specific band is produced. In this case, the exciton may be a singlet exciton, and may also be a triplet exciton. Accordingly, the light-emitting device 100 may provide light to the outside.

Meanwhile, the light-emitting device 100 may further include a first blocking layer (not illustrated) disposed between the first electrode 20 and the light-emitting layer 40 and/or a second blocking layer (not illustrated) disposed between the light-emitting layer 40 and the second electrode 50.

For example, the first blocking layer may be an electron blocking layer (EBL) which is disposed between the hole transport layer 30 and the light-emitting layer 40 and thus prevents electrons injected from the second electrode 50 from flowing into the hole transport layer 30 via the light-emitting layer 40. In addition, the first blocking layer may be an exciton blocking layer which prevents an exciton formed in the light-emitting layer 40 from being diffused in a direction of the first electrode 20 and thus being non-radiatively decayed.

In addition, the first blocking layer may be an exciton dissociation blocking layer (EDBL). The exciton dissociation blocking layer may prevent an exciton formed in the light-emitting layer from being non-radiatively decayed through the process of 'exciton dissociation' at the interface between the light-emitting layer 40 and the hole transport layer 30. In order to prevent exciton dissociation at the interface, a compound which forms the first blocking layer may be selected so as to have a HOMO value at a level similar to that of a compound which forms the light-emitting layer 40.

The second blocking layer may be a hole blocking layer (HBL) which is disposed between the light-emitting layer 40 and the second electrode 50, specifically, the light-emitting layer 40 and the electron transporting layer, and thus prevents holes from flowing into the electron transporting layer via the light-emitting layer 40 from the first electrode 20. Further, the second blocking layer may be an exciton blocking layer which prevents an exciton formed in the light-emitting layer 40 from being diffused in a direction of the second electrode 50 and thus being non-radiatively decayed.

When the thickness of each of the first and second blocking layers is adjusted so as to be suitable for the resonant length of the light-emitting device 100, the light-emitting efficiency may be increased, and the thickness may be adjusted such that the exciton may be formed in the central portion of the light-emitting layer 40 other than the interface between the light-emitting layer 40 and another layer.

FIG. 2 is a cross-sectional view for describing a light-emitting device according to another exemplary embodiment of the present invention.

Referring to FIG. 2, a light-emitting device 102 includes a first electrode 20, a hole transport layer 32, a light-emitting layer 40, and a second electrode 50, which are formed on a base substrate 10. Except for the hole transport layer 32, the other constituent elements are substantially the same as those described in FIG. 1, and thus the overlapping description thereof will be omitted.

As an example, the hole transport layer 32 may further include a P-type dopant together with a hole transport compound as a host material. The P-type dopant may include a P-type organic dopant and/or a P-type inorganic dopant.

Specific examples of the P-type organic dopant include compounds represented by the following Formulae 6 to 10, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), or tetracyanoquinodimethane (TCNQ), and the like. These may be used either alone or in combination of two or more thereof.

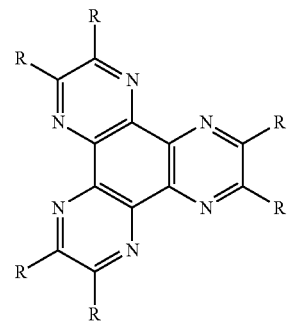

[Formula 6]

In Formula 6, R may represent a cyano group, a sulfone group, a sulfoxide group, a sulfonamide group, a sulfonate group, a nitro group, or a trifluoromethyl group.

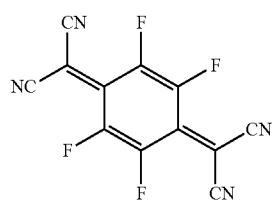

[Formula 7]

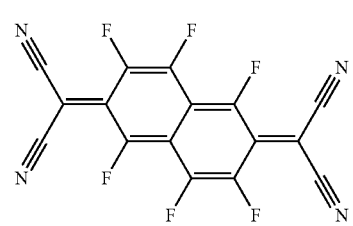

[Formula 8]

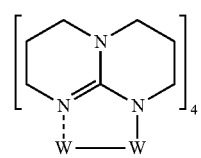

[Formula 9]

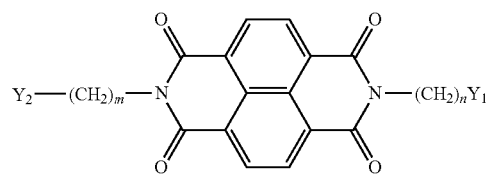

[Formula 10]

In Formula 10, m and n each independently represent an integer of 1 to 5, and $Y_1$ and $Y_2$ may each independently represent an aryl group having 6 to 20 carbon atoms, or a heteroaryl group having 2 to 20 carbon atoms. In this case, a hydrogen atom of the aryl group or heteroaryl group represented by $Y_1$ and $Y_2$ may be unsubstituted or substituted with an alkyl group having 1 to 5 carbon atoms, an alkoxy group having 1 to 5 carbon atoms, or a hydroxyl group, and hydrogen atoms of substituted or unsubstituted $Y_1$ and $Y_2$ may be each independently unsubstituted or substituted with a halogen group.

For example, the compound represented by Formula 10 may include a compound represented by the following Formula 10a or the following Formula 10b.

[Formula 10a]

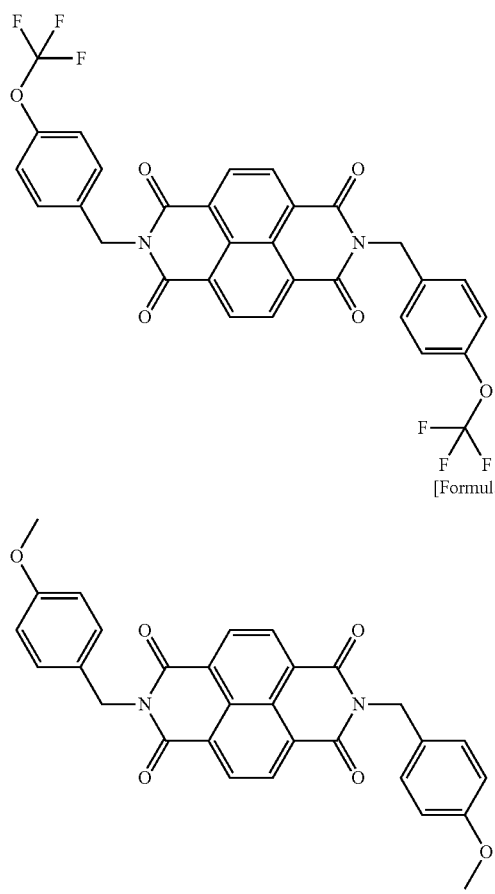

[Formula 10b]

Examples of the P-type inorganic dopant include metal oxide or metal halide, and the like. Specific examples of the P-type inorganic dopant include $MoO_3$, $V_2O_5$, $WO_3$, $SnO_2$, $ZnO$, $MnO_2$, $CoO_2$, $ReO_3$, $TiO_2$, $FeCl_3$, $SbCl_5$ or $MgF_2$, and the like. These may be used either alone or in combination of two or more thereof.

Meanwhile, the light-emitting device 102 may further include an interlayer (not illustrated). The interlayer may be disposed between the first electrode 20 and the hole transport layer 32. The interlayer may be formed of a compound used as the P-type dopant. Further, the light-emitting device 100 illustrated in FIG. 1 may also further include an interlayer disposed between the first electrode 20 and the hole transport layer 30.

As another example, the hole transport layer 32 may include a first layer and a second layer. The first layer is formed on the first electrode, and the second layer may be formed between the first layer and the light-emitting layer 40. In addition, the hole transport layer 32 may have a multi-layer structure having two or more layers, which includes the first and second layers.

The first layer may include a first hole transport compound as a host material and the P-type dopant described above as a dopant. The second layer may be composed of a second hole transport compound. In this case, the first hole transport compound and the second hole transport compound may be the same as or different from each other. However, when the first and second hole transport compounds are the same as each other, physical and chemical defects, which may be generated at the interface between heterogeneous materials, may be reduced to facilitate the injection of holes into the light-emitting layer. Further, when the first and second hole transport compounds are the same as each other, there is an advantage in that the manufacturing process is simplified and the manufacturing time may be reduced because the first layer and the second layer may be continuously formed in one chamber. Furthermore, physical properties such as the glass transition temperature become similar to each other between the adjacent layers, so that there is also an advantage in that durability of the device may be improved.

As another example, the first layer of the hole transport layer 32 includes a first hole transport compound and a first dopant, and the second layer may include a second hole transport compound and a second dopant. The first and second hole transport compounds may be the same as or different from each other.

Even as the first and second dopants, the same kinds of compounds may be used, or the different kinds of compounds may be used. When the first and second dopants include the same kinds of compounds, the content of the first dopant may be substantially the same as or higher than the content of the second dopant. The content of the first dopant is based on the total weight of the first hole transport compound, and the content of the second dopant is based on the total weight of the second hole transport compound.

In addition, although not illustrated in the drawing, the light-emitting device 102 may further include an electron transporting layer, an electron injecting layer, a first blocking layer, and/or a second blocking layer. The respective layers are substantially the same as those described in FIG. 1, and thus the overlapping specific description thereof will be omitted.

FIG. 3 is a cross-sectional view for describing a light-emitting device according to still another exemplary embodiment of the present invention.

Referring to FIG. 3, a light-emitting device 104 includes a first electrode 20, a hole transport layer 34, a light-emitting layer 40, an electron transporting layer 60, and a second electrode 50, which are formed on a base substrate 10. The light-emitting device 104 may further include an electron injecting layer (not illustrated) disposed between the electron transporting layer 60 and the second electrode 50.

The first electrode 20, the hole transport layer 34, and the second electrode 50 are substantially the same as those described in FIGS. 1 and 2. Therefore, the overlapping specific description thereof will be omitted.

The light-emitting layer 40 may be formed by combining various commercially available compounds in various compositions. The light-emitting layer 40 may include a host compound and a dopant compound which is a light-emitting material. In this case, it is possible to include the compound(s) represented by Formula 4 and/or Formula 5 as the host compound of the light-emitting layer 40.

The electron transporting layer 60 includes a compound represented by the following Formula 3.

[Formula 3]

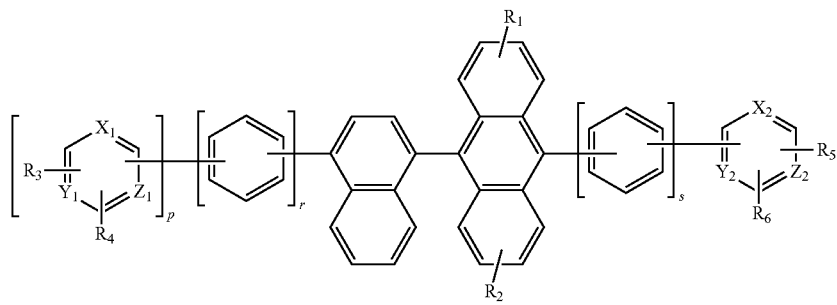

The compound represented by Formula 3 is a novel compound according to the present invention and may be substantially the same as those described above. Accordingly, the overlapping specific description of each of $R_1$ to $R_6$, $X_1$, $X_2$, $Y_1$, $Y_2$, $Z_1$, $Z_2$, p, r, and s will be omitted.

Although not illustrated in the drawing, the light-emitting device 104 may further include a first blocking layer (not illustrated) disposed between the first electrode 20 and the light-emitting layer 40 and/or a second blocking layer (not illustrated) disposed between the light-emitting layer 40 and the second electrode 50. The specific descriptions of the first and second blocking layers are substantially the same as those described in FIG. 1, and thus, the overlapping description thereof will be omitted.

Each of the light-emitting devices 100, 102, and 104 described above includes the novel compound according to the present invention, which is represented by Formula 1, and thus the light-emitting devices 100, 102, and 104 may have improved light-emitting efficiency and increased lifespan.

FIGS. 1 to 3 illustrate that the light-emitting devices 100, 102, and 104 are directly formed on the base substrate 10, but a thin film transistor may be disposed as a driving device, which drives pixels, between the first electrode 20 and the base substrate 10 of each of the light-emitting devices 100, 102, and 104. In this case, the first electrode 20 may become a pixel electrode connected to the thin film transistor. When the first electrode 20 is a pixel electrode, the first electrodes 20 are disposed spaced apart from each other at each of a plurality of pixels, and a partition wall pattern formed along the edge of the first electrode 20 is formed on the base substrate 10, so that layers to be stacked on the first electrode 20, which are disposed on the pixels adjacent to each other may be isolated from each other. That is, although not illustrated in the drawings, the light-emitting devices 100, 102, and 104 may be used for a display device which displays an image without a backlight.

Furthermore, the light-emitting devices 100, 102, and 104 may be used as a lighting device.

As described above, the light-emitting devices 100, 102, and 104 exemplified in the present invention may be used for various electronic devices such as the display device or the lighting device.

EXAMPLES

Hereinafter, novel compounds according to the present invention will be described in more detail through the specific Examples according to the present invention. The Examples to be exemplified below are only provided for the detailed description of the invention, but are not intended to limit the right scope thereby.

Example 1

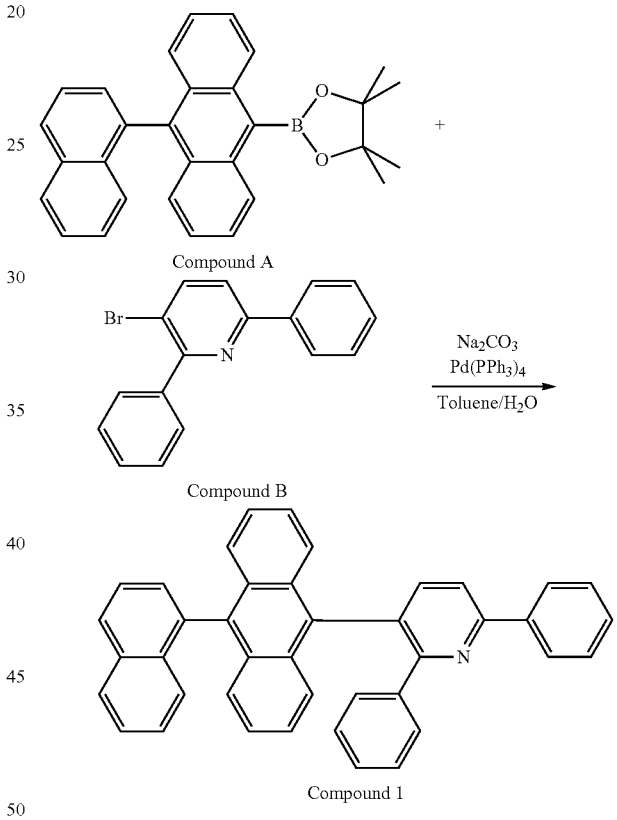

A 250 mL three-neck round-bottom flask was filled with nitrogen, and then Compound A (23.24 mmol, 10.0 g), Compound B (25.56 mmol, 7.93 g), and 100 mL of toluene were added thereto, and the resulting mixture was stirred for 30 minutes. Further, sodium carbonate ($Na_2CO_3$) (58.09 mmol, 8.03 g) was dissolved in 50 mL of water ($H_2O$), and then the resulting solution was added to the 250 mL three-neck round-bottom flask. Subsequently, tetrakis(triphenylphosphine)palladium ($Pd(PPh_3)_4$) (0.93 mmol, 1.07 g) was added to the 250 mL three-neck round-bottom flask, and then the resulting mixture was refluxed for 48 hours while the light was blocked.

The reaction mixture was cooled, and then extracted by using ethyl acetate (EA) and distilled water, concentrated, and then dissolved in 50 mL of tetrahydrofuran (THF), and the resulting solution was added to a 1 L container contain-

Example 2

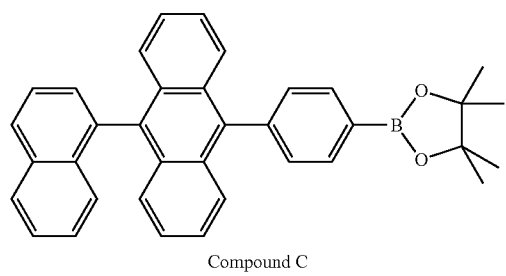

Compound C

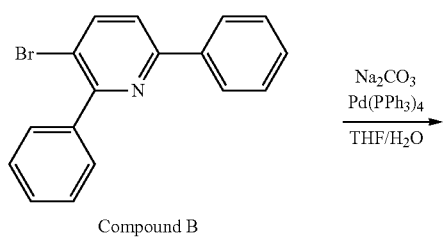

Compound B

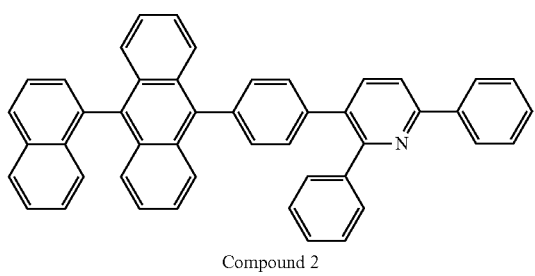

Compound 2

A 500 mL three-neck round-bottom flask was filled with nitrogen, and then Compound C (23.69 mmol, 12.0 g), Compound B (26.06 mmol, 8.09 g), and 200 mL of tetrahydrofuran (THF) were added thereto, and the resulting mixture was stirred for 30 minutes. Further, sodium carbonate ($Na_2CO_3$) (94.78 mmol, 13.10 g) was dissolved in 100 mL of water ($H_2O$), and then the resulting solution was added to the 500 mL three-neck round-bottom flask. Subsequently, tetrakis(triphenylphosphine)palladium ($Pd(PPh_3)_4$) (0.948 mmol, 1.1 g) was added to the 500 mL three-neck round-bottom flask, and then the resulting mixture was refluxed for 12 hours while light was blocked.

The reaction mixture was cooled, and then added to a 1 L container containing 500 mL of methanol, and then the resulting solution was stirred for 20 minutes. The resulting product was filtered to obtain about 12.9 g of pale yellow solid Compound 2 (yield 90%).

MALDI-TOF: m/z=609.0524 ($C_{47}H_{31}N$=609.2)

Example 3

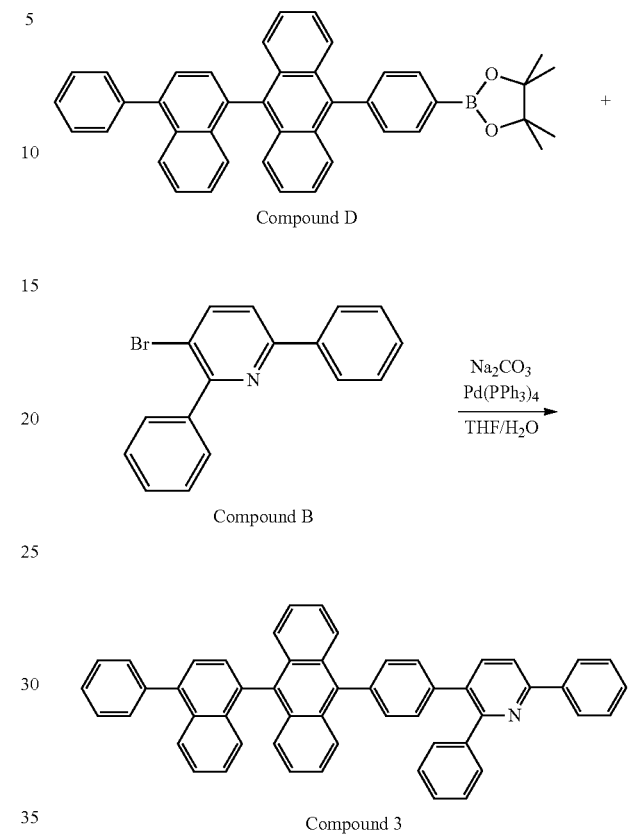

A 500 mL three-neck round-bottom flask was filled with nitrogen, and then Compound D (25.76 mmol, 15.0 g), Compound B (28.33 mmol, 8.79 g), and 240 mL of tetrahydrofuran (THF) were added thereto, and the resulting mixture was stirred for 30 minutes. Further, sodium carbonate ($Na_2CO_3$) (103.04 mmol, 14.24 g) was dissolved in 120 mL of water ($H_2O$), and then the resulting solution was added to the 500 mL three-neck round-bottom flask. Subsequently, tetrakis(triphenylphosphine)palladium ($Pd(PPh_3)_4$) (1.03 mmol, 1.2 g) was added to the 500 mL three-neck round-bottom flask, and then the resulting mixture was refluxed for 12 hours while light was blocked.

The reaction mixture was cooled, and then added to a 1 L container containing 500 mL of methanol, and then the resulting solution was stirred for 20 minutes. The resulting product was filtered to obtain about 15.0 g of white solid Compound 3 (yield 85%).

MALDI-TOF: m/z=685.2596 ($C_{53}H_{35}N$=685.3)

Comparative Examples 1 to 2

The compounds represented by the following Formulae a and b were prepared based on those disclosed in Japanese Patent Application Laid-Open No. 2012-067077, and were used as compounds of Comparative Examples 1 and 2, respectively.

--- ing 500 mL of methanol, and the resulting mixture was stirred for 20 minutes. The resulting product was filtered to obtain about 8.68 g of pale gray solid Compound 1 (yield 70%).

MALDI-TOF: m/z=533.1586 ($C_{41}H_{27}N$=533.20)

[Formula a]

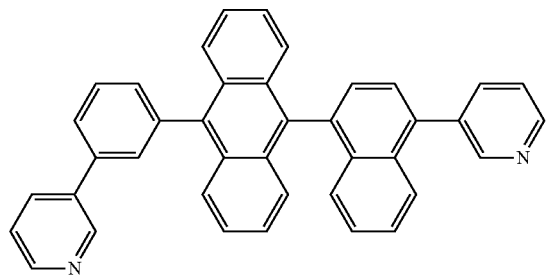

[Formula b]

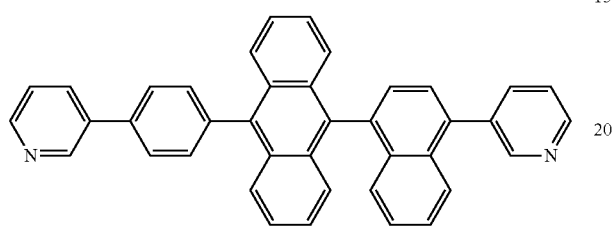

Manufacture of Light-Emitting Devices A-1 to A-3

A compound (HAT-CN) represented by the following Formula 11 was deposited on a first electrode formed of indium tin oxide (ITO), thereby forming a first layer having a thickness of 100 Å. A compound (NPB, (N,N'-bis(1-naphthyl)-N,N'-diphenyl-1,1'-biphenyl-4,4'-diamine)) represented by the following Formula 12 was deposited to have a thickness of 300 Å on the first layer, thereby forming a second layer.

A compound represented by the following Formula 13 as a light-emitting host compound and a compound represented by the following Formula 14 as a light-emitting dopant compound were co-deposited at a weight ratio of 100:5 on the second layer, thereby forming a light-emitting layer having a thickness of about 200 Å.

And then, the compound according to Example 1 of the present invention was deposited on the light-emitting layer, thereby forming an electron transporting layer having a thickness of about 360 Å. Subsequently, an electron injecting layer having a thickness of about 10 Å was formed on the electron transporting layer by using Liq represented by the following Formula 15.

A second electrode using an aluminum thin film having a thickness of 1,000 Å was formed on the electron injecting layer.

[Formula 11]

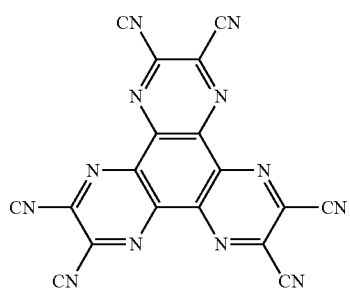

[Formula 12]

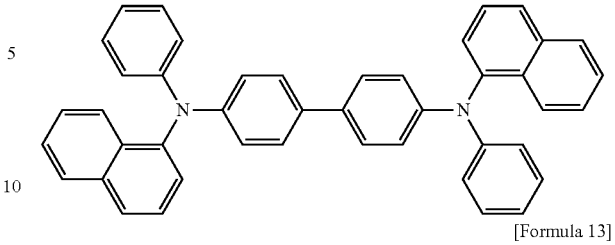

[Formula 13]

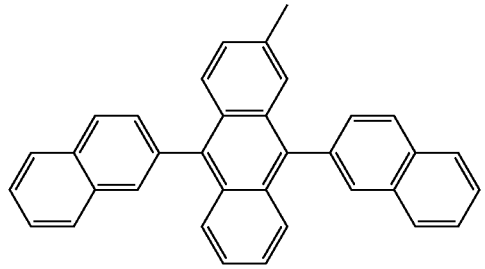

[Formula 14]

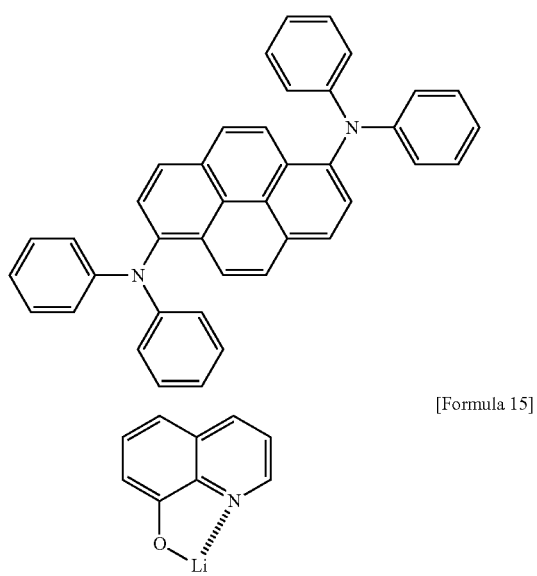

[Formula 15]

Blue light-Emitting Device A-1 including the compound according to Example 1 of the present invention was manufactured by the above method.

Further, Light-Emitting Devices A-2 and A-3 were manufactured through a process which is substantially the same as the process of manufacturing Light-Emitting Device A-1, except that the electron transporting layer was formed of each of the compounds according to Examples 2 and 3 of the present invention.

Manufacture of Comparative Devices 1 and 2

Comparative Devices 1 and 2 were manufactured through a process which is substantially the same as the process of manufacturing Light-Emitting Device A-1, except that the electron transporting layer was formed by using each of the compounds according to Comparative Examples 1 and 2.

Evaluation of Power Efficiency and Lifespan of Light-Emitting Device

For each of Light-Emitting Devices A-1 to A-3 and Comparative Devices 1 and 2, a sealant for UV curing was dispensed at the edge of a cover glass, to which a moisture absorbent (Getter) was attached, in a glove box under a nitrogen atmosphere, and then each of the light-emitting devices and the comparative devices was cohered to the cover glass, and the sealant was cured by irradiating UV light thereon. For each of Light-Emitting Devices A-1 to A-3 and Comparative Devices 1 and 2 thus prepared above, the consumption efficiency was measured based on the value when the brightness was 1,000 cd/m$^2$. The unit of the result of measuring the power efficiency was lm/W. In addition, the color coordinate was measured based on CIE 1931. The results are shown in Table 4.

Furthermore, the lifespan of each of Light-Emitting Devices A-1 to A-3 and Comparative Devices 1 and 2 was measured by using a lifespan measurement device provided in a measurement oven which was constantly maintained at a temperature of 25° C. $T_{50}$ means a time for the brightness of the light-emitting device to become 50% as compared to the initial brightness when the initial brightness of the light-emitting device is 5,000 cd/m$^2$. The results are shown in Table 6.

The value for the lifespan may be converted into a lifespan which is expected in the case where the measurement is made under other measurement conditions based on the conversion equation publicly known to the person skilled in the art.

TABLE 6

| Device No. | Power efficiency [lm/W] | Lifespan ($T_{50}$ [hr]) | Color coordinate (X, Y) |
|---|---|---|---|
| Light-Emitting Device A-1 | 7.1 | 221 | 0.150, 0.155 |
| Light-Emitting Device A-2 | 7.2 | 243 | 0.149, 0.157 |
| Light-Emitting Device A-3 | 7.6 | 261 | 0.148, 0.158 |
| Comparative Device 1 | 5.3 | 143 | 0.153, 0.163 |
| Comparative Device 2 | 4.9 | 121 | 0.152, 0.161 |

Referring to Table 6, it can be seen that the power efficiencies of Light-Emitting Devices A-1 to A-3, which include the electron transporting layer formed of each of the compounds according to Examples 1 to 3 of the present invention, are 7.1 lm/W or more, and the average power efficiency is about 7.3 lm/W. When compared to the result that the power efficiency of Comparative Device 1 was 5.3 lm/W, the power efficiency of Comparative Device 2 was 4.9 lm/W, and the average power efficiency of Comparative Devices 1 and 2 was about 5.1 lm/W, it can be seen that the power efficiencies of Light-Emitting Devices A-1 to A-3 including the compounds according to Examples 1 to 3 of the present invention have been significantly increased. For example, it can be seen that the power efficiency of Light-Emitting Device A-3 is improved by about 43% compared to that of Comparative Device 1.

Further, it can be seen that the lifespans of Light-Emitting Devices A-1 to A-3 are 221 hours, 243 hours, and 261 hours, respectively, and the average device lifespan thereof is about 242 hours, whereas the lifespans of Comparative Devices 1 and 2 are 143 hours and 121 hours, respectively, and the average device lifespan thereof is about 132 hours. Accordingly, it can be seen that the lifespans of Light-Emitting Devices A-1 to A-3 including the compounds according to Examples 1 to 3 of the present invention are increased by at least 100 hours compared to the lifespans of Comparative Devices 1 and 2. For example, it can be seen that the lifespan of Light-Emitting Device A-3 is increased by about 83% compared to that of Comparative Device 1.

Meanwhile, it can be seen that when the color coordinates of Light-Emitting Devices A-1 to A-3 based on CIE 1931 are compared to those of Comparative Devices 1 and 2 based on CIE 1931, Light-Emitting Devices A-1 to A-3 emit light having a blue color substantially the same as Comparative Devices 1 and 2. That is, it can be seen that when the compounds according to Examples 1 to 3 of the present invention are applied to the electron transporting layer of the blue light-emitting device, the blue light-emitting device has little variation in the color coordinate while having improved power efficiency and increased lifespan.

Manufacture of Light-Emitting Devices B-1 to B-3

The compound represented by Formula 12 and the compound (HAT-CN) represented by Formula 11 were co-deposited at a weight ratio of 100:3 on a first electrode formed of indium tin oxide (ITO), thereby forming a first layer having a thickness of 100 Å. The compound represented by Formula 12 was deposited to have a thickness of 300 Å on the first layer, thereby forming a second layer.

The compound represented by Formula 13 as a light-emitting host compound and the compound represented by Formula 14 as a light-emitting dopant compound were co-deposited at a weight ratio of 100:5 on the second layer, thereby forming a light-emitting layer having a thickness of about 200 Å.

And then, the compound according to Example 1 and Liq represented by Formula 15 as the host compounds of the electron transporting layer were co-deposited at a weight ratio of 50:50 on the light-emitting layer, thereby forming an electron transporting layer having a thickness of about 360 Å. Subsequently, an electron injecting layer having a thickness of about 5 Å was formed on the electron transporting layer by using Liq represented by Formula 15.

A second electrode using an aluminum thin film having a thickness of 1,000 Å was formed on the electron injecting layer.

Blue Light-Emitting Device B-1 including the compound according to Example 1 of the present invention was manufactured by the above method.

In addition, Light-Emitting Devices B-2 and B-3 were manufactured through a process which is substantially the same as the process of manufacturing Light-Emitting Device B-1, except that the compounds according to Examples 2 and 3 were each used as the host compound of the electron transporting layer.

Manufacture of Comparative Devices 3 and 4

Comparative Devices 3 and 4 were manufactured through a process which is substantially the same as the process of manufacturing Light-Emitting Device B-1, except that the electron transporting layer was formed by using each of the compounds according to Comparative Examples 1 and 2 as the host compound of the electron transporting layer.

Evaluation of Power Efficiency and Lifespan of Light-Emitting Device

For each of Light-Emitting Devices B-1 to B-3 and Comparative Devices 3 and 4, an experiment, which is substantially the same as the experiment in which the power efficiency, lifespan, and color coordinate of Light-Emitting Devices A-1 to A-3 and Comparative Devices 1 and 2 were evaluated, was performed. The results are shown in Table 7.

TABLE 7

| Device No. | Power efficiency [lm/W] | Lifespan ($T_{50}$ [hr]) | Color coordinate (X, Y) |
|---|---|---|---|
| Light-emitting Device B-1 | 7.5 | 258 | 0.148, 0.152 |
| Light-emitting Device B-2 | 7.9 | 274 | 0.149, 0.153 |
| Light-emitting Device B-3 | 8.6 | 289 | 0.149, 0.157 |
| Comparative Device 3 | 6.2 | 189 | 0.151, 0.152 |
| Comparative Device 4 | 5.4 | 139 | 0.154, 0.151 |

Referring to Table 7, it can be seen that the power efficiencies of Light-Emitting Devices B-1 to B-3 are 7.5 lm/W, 7.9 lm/W, and 8.6 lm/W, respectively, and the average power efficiency thereof is about 8.0 lm/W. In contrast, it can be seen that the power efficiencies of Comparative Devices 3 and 4 are 6.2 lm/W and 5.4 lm/W, respectively. Accordingly, it can be seen that the power efficiencies of Light-Emitting Devices B-1 to B-3 including the compounds according to Examples 1 to 3 of the present invention are significantly increased compared to those of Comparative Devices 3 and 4. For example, it can be seen that the power efficiency of Light-Emitting Device B-3 is improved by about 39% compared to that of Comparative Device 3.

In addition, it can be seen that the lifespans of Light-Emitting Devices B-1 to B-3 are 258 hours, 274 hours, and 289 hours, respectively, and the average device lifespan thereof is about 274 hours. In contrast, it can be seen that the lifespans of Comparative Devices 3 and 4 are 189 hours and 139 hours, respectively. Accordingly, it can be seen that the lifespans of Light-Emitting Devices B-1 to B-3 including the compounds according to Examples 1 to 3 of the present invention are significantly increased compared to those of Comparative Devices 3 and 4. For example, it can be seen that the lifespan of Light-emitting Device B-3 is increased by about 53% compared to that of Comparative Device 3.

Meanwhile, it can be seen that when the color coordinates of Light-Emitting Devices B-1 to B-3 based on CIE 1931 are compared to the color coordinates of Comparative Devices 3 and 4 based on CIE 1931, Light-Emitting Devices B-1 to B-3 emit light having a blue color substantially the same as Comparative Devices 3 and 4. That is, it can be seen that when the compounds according to Examples 1 to 3 of the present invention are applied to the electron transporting layer of the blue light-emitting device, the blue light-emitting device has little variation in the color coordinate while having improved power efficiency and increased lifespan.

Example 4

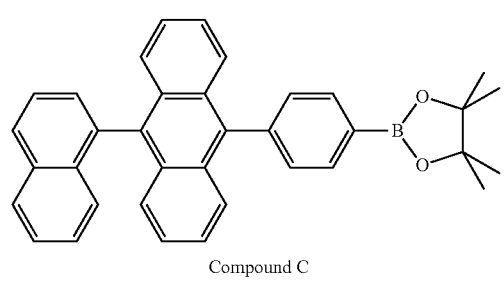

Compound C

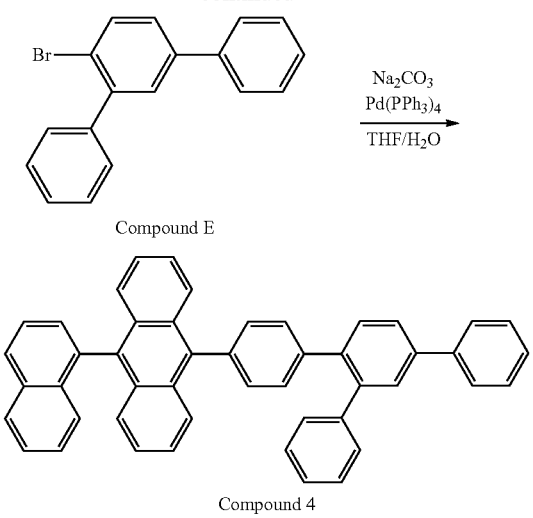

Compound E

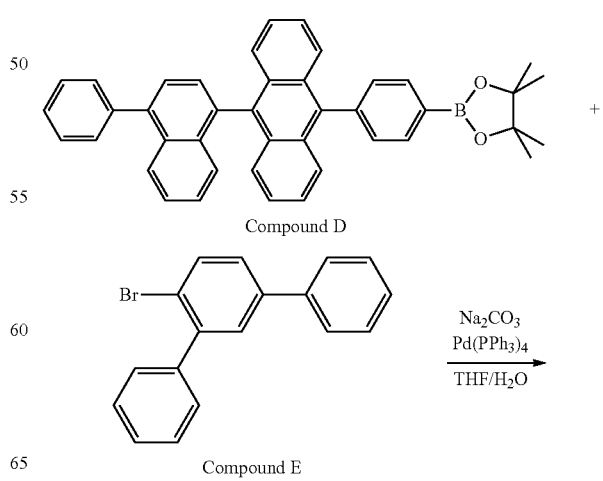

Compound 4

A 500 mL three-neck round-bottom flask was filled with nitrogen, and then Compound C (19.74 mmol, 10.0 g), Compound E (21.72 mmol, 6.72 g), and 160 mL of tetrahydrofuran (THF) were added thereto, and the resulting mixture was stirred for 30 minutes. Further, sodium carbonate ($Na_2CO_3$) (78.98 mmol, 10.92 g) was dissolved in 80 mL of water ($H_2O$), and then the resulting solution was added to the 500 mL three-neck round-bottom flask. Subsequently, tetrakis(triphenylphosphine)palladium ($Pd(PPh_3)_4$) (0.79 mmol, 0.9 g) was added to the 500 mL three-neck round-bottom flask, and then the resulting mixture was refluxed for 12 hours while light was blocked.

The reaction mixture was cooled, and then added to a 1 L container containing 300 mL of methanol, and then the resulting solution was stirred for 20 minutes. The resulting product was filtered to obtain about 10.8 g of pale gray solid Compound 4 (yield 90%).

MALDI-TOF: m/z=608.2587 ($C_{48}H_{32}$=608.3)

Example 5

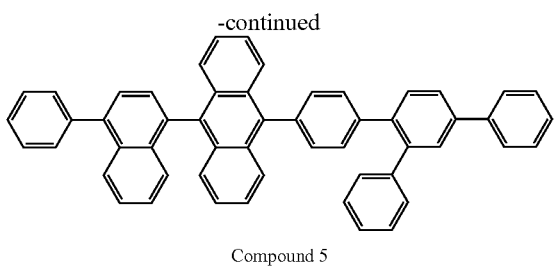

Compound 5

A 500 mL three-neck round-bottom flask was filled with nitrogen, and then Compound D (20.06 mmol, 12.0 g), Compound E (22.66 mmol, 7.01 g), and 200 mL of tetrahydrofuran (THF) were added thereto, and the resulting mixture was stirred for 30 minutes. Further, sodium carbonate ($Na_2CO_3$) (82.43 mmol, 11.39 g) was dissolved in 100 mL of water ($H_2O$), and then the resulting solution was added to the 500 mL three-neck round-bottom flask. Subsequently, tetrakis(triphenylphosphine)palladium ($Pd(PPh_3)_4$) (0.824 mmol, 0.95 g) was added to the 500 mL three-neck round-bottom flask, and then the resulting mixture was refluxed for 12 hours while light was blocked.

The reaction mixture was cooled, and then added to a 1 L container containing 500 mL of methanol, and then the resulting solution was stirred for 20 minutes. The resulting product was filtered to obtain about 11.2 g of white solid Compound 5 (yield 80%).

MALDI-TOF: m/z=684.0045 ($C_{54}H_{36}$=684.3)

Example 6

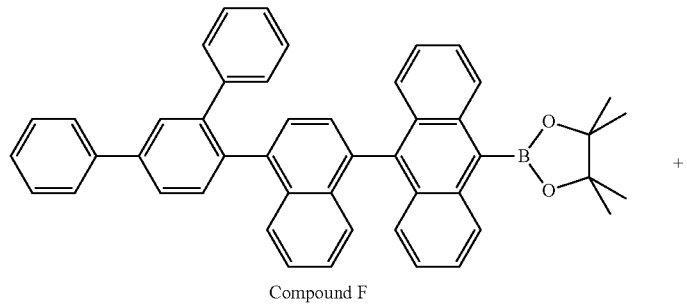

Compound F

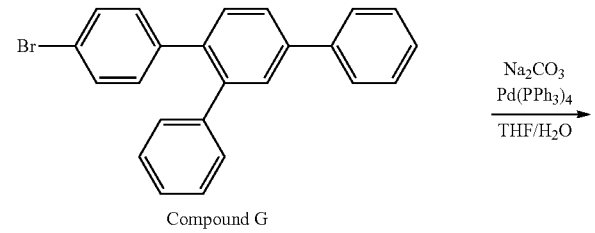

Compound G

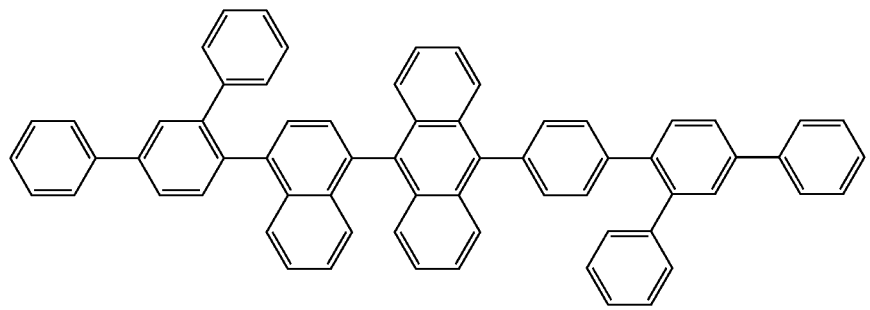

Compound 6

A 500 mL three-neck round-bottom flask was filled with nitrogen, and then Compound F (15.18 mmol, 10.0 g), Compound G (16.70 mmol, 6.44 g), and 160 mL of tetrahydrofuran (THF) were added thereto, and the resulting mixture was stirred for 30 minutes. Further, sodium carbonate ($Na_2CO_3$) (60.73 mmol, 8.39 g) was dissolved in 100 mL of water ($H_2O$), and then the resulting solution was added to the 500 mL three-neck round-bottom flask. Subsequently, tetrakis(triphenylphosphine)palladium ($Pd(PPh_3)_4$) (0.607 mmol, 0.70 g) was added to the 500 mL three-neck round-bottom flask, and then the resulting mixture was refluxed for 18 hours while light was blocked.

The reaction mixture was cooled, and then added to a 1 L container containing 300 mL of methanol, and then the resulting solution was stirred for 30 minutes. The resulting product was filtered to obtain about 8.9 g of pale brown solid Compound 6 (yield 70%).

MALDI-TOF: m/z=836.3812 ($C_{66}H_{44}$=836.3)

Example 7

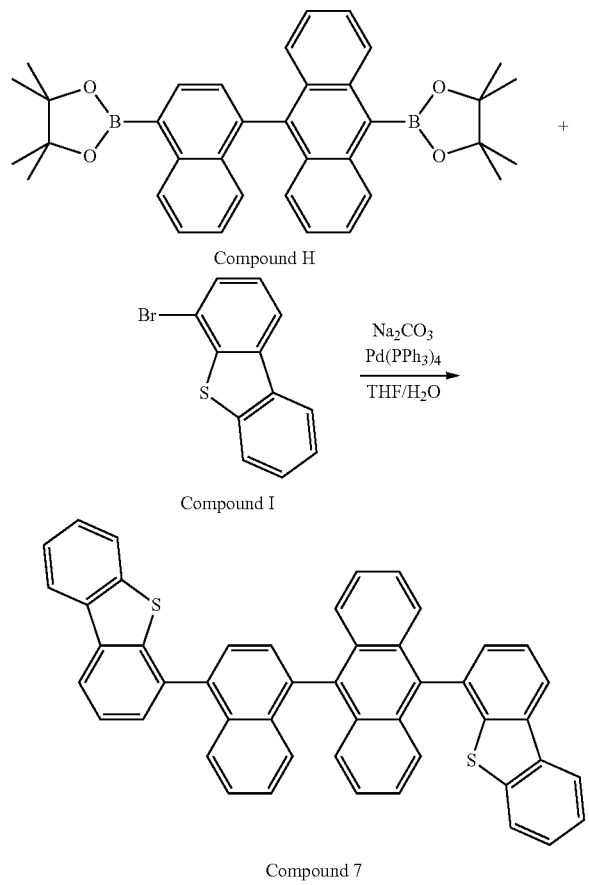

Compound 7

A 1 L three-neck round-bottom flask was filled with nitrogen, and then Compound H (26.96 mmol, 15.0 g), Compound I (59.32 mmol, 15.6 g), and 240 mL of tetrahydrofuran (THF) were added thereto, and the resulting mixture was stirred for 30 minutes. Further, sodium carbonate ($Na_2CO_3$) (215.71 mmol, 29.81 g) was dissolved in 120 mL of water ($H_2O$), and then the resulting solution was added to the 1 L three-neck round-bottom flask. Subsequently, tetrakis(triphenylphosphine)palladium ($Pd(PPh_3)_4$) (2.157 mmol, 2.49 g) was added to the 1 L three-neck round-bottom flask, and then the resulting mixture was refluxed for 24 hours while light was blocked.

The reaction mixture was cooled, and then added to a 1 L container containing 500 mL of methanol, and then the resulting solution was stirred for 30 minutes. The resulting product was filtered to obtain about 14 g of pale gray solid Compound 7 (yield 77%).

MALDI-TOF: m/z=668.1059 ($C_{48}H_{28}S_2$=668.2)

Example 8

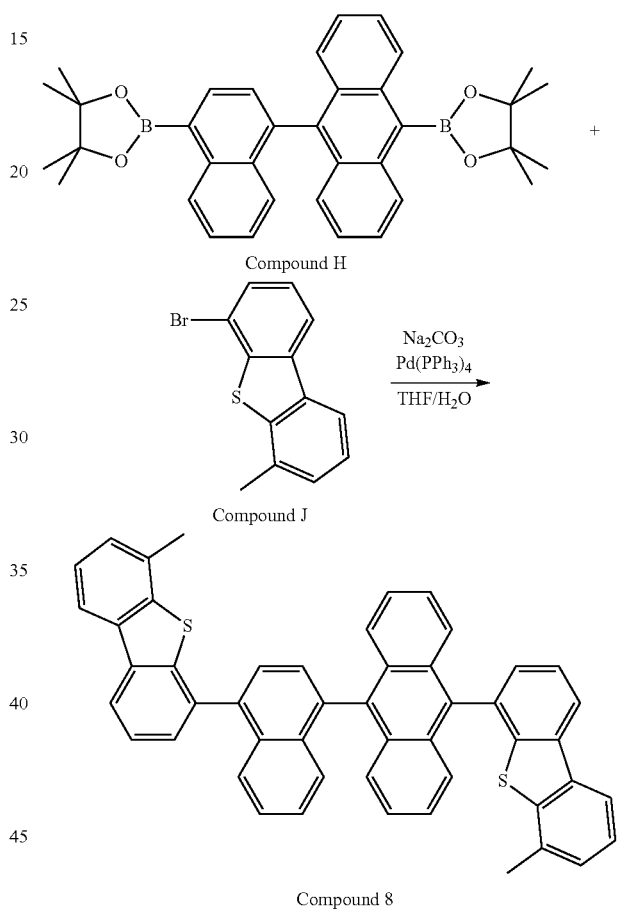

Compound 8

A 1 L three-neck round-bottom flask was filled with nitrogen, and then Compound H (26.96 mmol, 15.0 g), Compound J (59.32 mmol, 16.4 g), and 240 mL of tetrahydrofuran (THF) were added thereto, and the resulting mixture was stirred for 30 minutes. Further, sodium carbonate ($Na_2CO_3$) (215.71 mmol, 29.81 g) was dissolved in 120 mL of water ($H_2O$), and then the resulting solution was added to the 1 L three-neck round-bottom flask. Subsequently, tetrakis(triphenylphosphine)palladium ($Pd(PPh_3)_4$) (2.157 mmol, 2.49 g) was added to the 1 L three-neck round-bottom flask, and then the resulting mixture was refluxed for 24 hours while light was blocked.

The reaction mixture was cooled, and then added to a 1 L container containing 500 mL of methanol, and then the resulting solution was stirred for 30 minutes. The resulting product was filtered to obtain about 13.5 g of pale gray solid Compound 8 (yield 72%).

MALDI-TOF: m/z=696.3105 ($C_{50}H_{32}S_2$=696.2)

Example 9

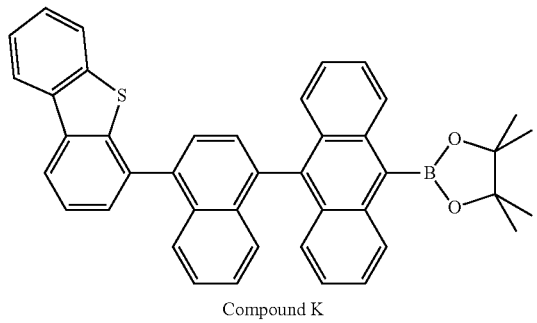

Compound K

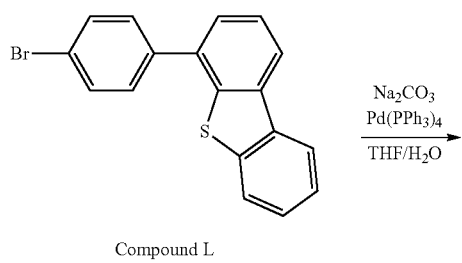

Compound L

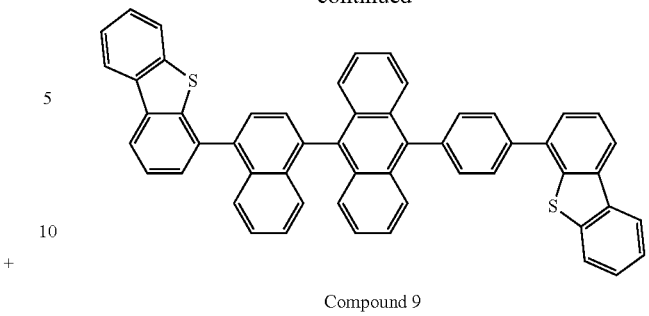

Compound 9

A 1 L three-neck round-bottom flask was filled with nitrogen, and then Compound K (24.48 mmol, 15.0 g), Compound L (26.93 mmol, 9.14 g), and 240 mL of tetrahydrofuran (THF) were added thereto, and the resulting mixture was stirred for 30 minutes. Further, sodium carbonate ($Na_2CO_3$) (97.94 mmol, 13.54 g) was dissolved in 120 mL of water ($H_2O$), and then the resulting solution was added to the 1 L three-neck round-bottom flask. Subsequently, tetrakis(triphenylphosphine)palladium ($Pd(PPh_3)_4$) (0.979 mmol, 1.13 g) was added to the 1 L three-neck round-bottom flask, and then the resulting mixture was refluxed for 24 hours while light was blocked.

The reaction mixture was cooled, and then added to a 1 L container containing 500 mL of methanol, and then the resulting solution was stirred for 20 minutes. The resulting product was filtered to obtain about 15.2 g of pale green solid Compound 9 (yield 84%).

MALDI-TOF: m/z=744.1958 ($C_{54}H_{32}S_2$=744.2)

Example 10

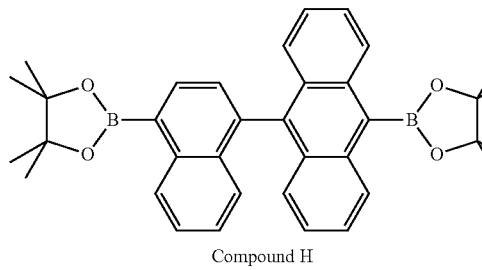

Compound H

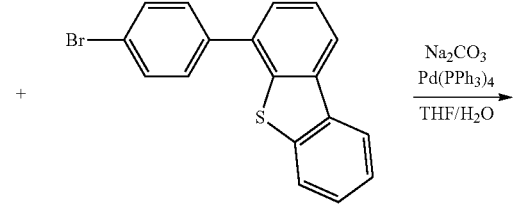

Compound L

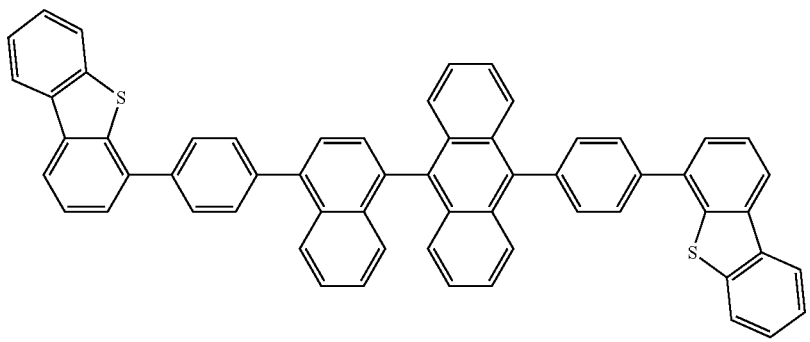

Compound 10

A 500 mL three-neck round-bottom flask was filled with nitrogen, and then Compound H (21.57 mmol, 12.0 g), Compound L (47.45 mmol, 16.1 g), and 200 mL of tetrahydrofuran (THF) were added thereto, and the resulting mixture was stirred for 30 minutes. Further, sodium carbonate ($Na_2CO_3$) (172.5 mmol, 23.85 g) was dissolved in 100 mL of water ($H_2O$), and then the resulting solution was added to the 500 mL three-neck round-bottom flask. Subsequently, tetrakis(triphenylphosphine)palladium ($Pd(PPh_3)_4$) (1.7 mmol, 1.99 g) was added to the 500 mL three-neck round-bottom flask, and then the resulting mixture was refluxed for 24 hours while light was blocked.

The reaction mixture was cooled, and then added to a 1 L container containing 300 mL of methanol, and then the resulting solution was stirred for 30 minutes. The resulting product was filtered to obtain about 14.5 g of pale gray solid Compound 10 (yield 82%).

MALDI-TOF: m/z=821.3564 ($C_{60}H_{36}S_2$=820.2)

Comparative Examples 3 to 8

A compound represented by the following Formula c, a compound represented by the following Formula d, a compound represented by the following Formula e, the compound represented by the following Formula f, a compound represented by the following Formula g, and a compound represented by the following Formula h were prepared based on those disclosed in PCT International Publication No. WO2009-107596, PCT International Publication No. WO2006-098080, Korean Patent Application Laid-Open No. 2010-0001984, Japanese Patent No. 4807013, PCT International Publication No. WO2006-104044, and Korean Patent Application Laid-Open No. 2009-133071, respectively, and were used as compounds of Comparative Examples 3 to 8, respectively.

[Formula c]

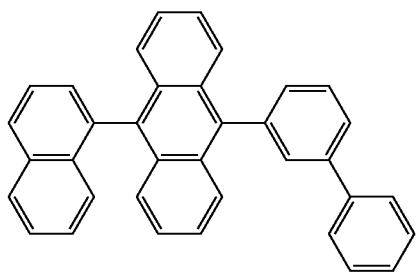

[Formula d]

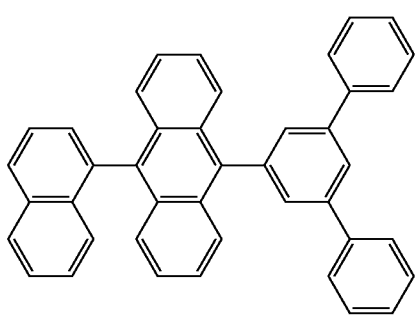

[Formula e]

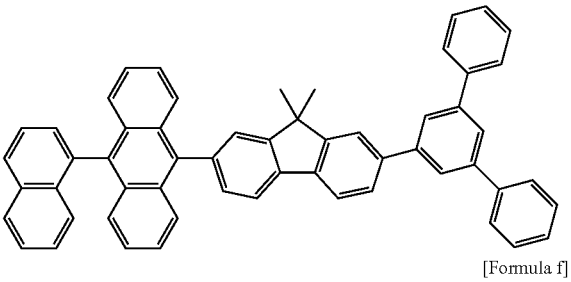

[Formula f]

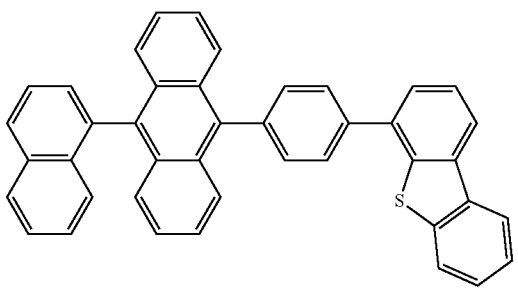

[Formula g]

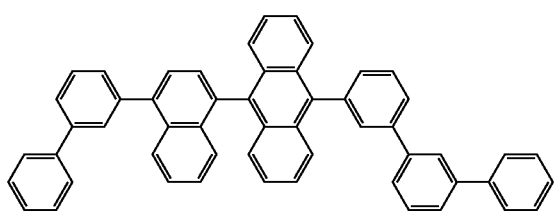

[Formula h]

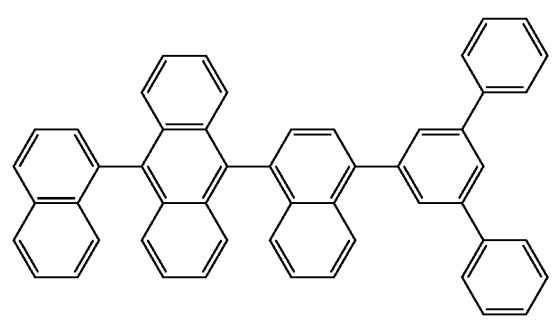

Manufacture of Light-Emitting Devices C-1 to C-7

The compound (HAT-CN) represented by Formula 11 was deposited on a first electrode formed of indium tin oxide (ITO), thereby forming a first layer having a thickness of 100 Å. The compound represented by Formula 12 was deposited to have a thickness of 300 Å on the first layer, thereby forming a second layer.

The compound according to Example 4 of the present invention as a light-emitting host compound and the compound represented by Formula 14 as a light-emitting dopant compound were co-deposited at a weight ratio of 100:5 on the second layer, thereby forming a light-emitting layer having a thickness of about 200 Å.

And then, a compound represented by the following Formula 16 and Liq represented by Formula 15 were co-deposited at a weight ratio of 50:50 on the light-emitting layer, thereby forming an electron transporting layer having a thickness of about 360 Å. Subsequently, an electron injecting layer having a thickness of about 5 Å was formed on the electron transporting layer by using Liq represented by Formula 15.

A second electrode using an aluminum thin film having a thickness of 1,000 Å was formed on the electron injecting layer.

[Formula 16]

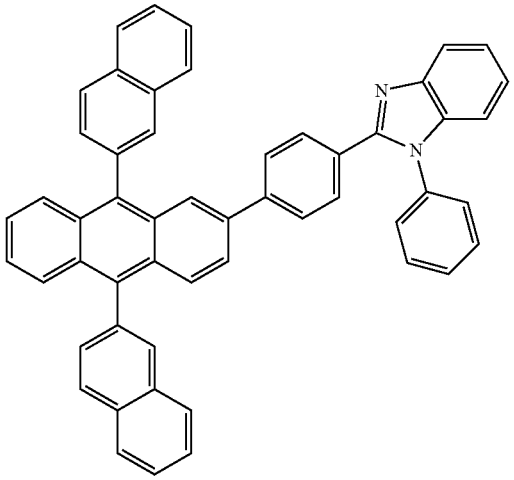

Blue Light-Emitting Device C-1 including the compound according to Example 4 of the present invention was manufactured by the above method.

Further, Light-Emitting Devices C-2 to C-7 were manufactured through a process which is substantially the same as the process of manufacturing Light-Emitting Device C-1, except that as the host compound of the light-emitting layer, each of the compounds according to Examples 5 to 10 of the present invention was used.

Manufacture of Comparative Devices 5 to 10

Comparative Devices 5 to 10 were manufactured through a process which is substantially the same as the process of manufacturing Light-Emitting Device C-1, except that as the host compound of the light-emitting layer, each of the compounds according to Comparative Examples 3 to 8 was used.

Evaluation of Power Efficiency and Lifespan of Light-Emitting Device

For each of Light-Emitting Devices C-1 to C-7 and Comparative Devices 5 to 10, an experiment, which is substantially the same as the experiment in which the power efficiency, lifespan, and color coordinate of Light-Emitting Devices A-1 to A-3 and Comparative Devices 1 and 2 were evaluated, was performed. The results are shown in Table 8.

TABLE 8

| Device No. | Power efficiency [lm/W] | Lifespan ($T_{50}$ [hr]) | Color coordinate (X, Y) |
| --- | --- | --- | --- |
| Light-Emitting Device C-1 | 7.1 | 224 | 0.147, 0.155 |
| Light-Emitting Device C-2 | 7.7 | 278 | 0.146, 0.151 |
| Light-Emitting Device C-3 | 6.9 | 220 | 0.145, 0.152 |
| Light-Emitting Device C-4 | 7.4 | 255 | 0.145, 0.153 |

TABLE 8-continued

| Device No. | Power efficiency [lm/W] | Lifespan ($T_{50}$ [hr]) | Color coordinate (X, Y) |
| --- | --- | --- | --- |
| Light-Emitting Device C-5 | 7.5 | 263 | 0.146, 0.153 |
| Light-Emitting Device C-6 | 7.3 | 247 | 0.143, 0.153 |
| Light-Emitting Device C-7 | 6.8 | 214 | 0.146, 0.151 |
| Comparative Device 5 | 5.1 | 159 | 0.157, 0.162 |
| Comparative Device 6 | 4.9 | 147 | 0.157, 0.163 |
| Comparative Device 7 | 3.6 | 87 | 0.157, 0.161 |
| Comparative Device 8 | 4.8 | 131 | 0.159, 0.162 |
| Comparative Device 9 | 3.8 | 98 | 0.155, 0.161 |
| Comparative Device 10 | 4.1 | 113 | 0.156, 0.161 |

Referring to Table 8, it can be seen that the power efficiencies of Light-Emitting Devices C-1 to C-7 are 7.1 lm/W, 7.7 lm/W, 6.9 lm/W, 7.4 lm/W, 7.5 lm/W, 7.3 lm/W, and 6.8 lm/W, respectively, and the average power efficiency thereof is 7.2 lm/W. In contrast, it can be seen that the average power efficiency of Comparative Devices 5 to 10 fails to reach 4.4 lm/W. Accordingly, it can be seen that the power efficiencies of Light-Emitting Devices C-1 to C-7 including the compound according to the present invention as a host compound of the light-emitting layer are increased by at least about 33% compared to the power efficiencies of Comparative Devices 5 to 10. In particular, it can be seen that the power efficiency of Light-Emitting Device C-2 is improved by about 51% compared to that of Comparative Device 5.

In addition, it can be seen that the lifespans of Light-Emitting Devices C-1 to C-7 are 224 hours, 278 hours, 220 hours, 255 hours, 263 hours, 247 hours, and 214 hours, respectively, and the average lifespan thereof is about 243 hours. In contrast, it can be seen that the lifespans of Comparative Devices 5 to 10 are 159 hours, 147 hours, 87 hours, 131 hours, 98 hours, and 113 hours, respectively, and the average lifespan thereof is about 123 hours. Accordingly, it can be seen that the lifespans of Light-Emitting Devices C-1 to C-7 including the compound according to the present invention as a host compound of the light-emitting layer are increased by at least about 34% compared to the lifespans of Comparative Devices 5 to 10. In particular, it can be seen that the lifespan of Light-Emitting Device C-2 is increased by about 75% compared to that of Comparative Device 5.

Meanwhile, it can be seen that when the color coordinates of Light-Emitting Devices C-1 to C-7 based on CIE 1931 are compared to the color coordinates of Comparative Devices 5 to 10 based on CIE 1931, Light-Emitting Devices C-1 to C-7 emit light having a blue color substantially the same as Comparative Devices 5 to 10. That is, it can be seen that when the compounds according to Examples 4 to 10 of the present invention are applied to the light-emitting layer of the blue light-emitting device as a host compound, the blue light-emitting device has little variation in the color coordinate while having improved power efficiency and increased lifespan.

Manufacture of Light-Emitting Devices D-1 to D-7

The compound represented by Formula 12 and the compound (HAT-CN) represented by Formula 11 were co-deposited at a weight ratio of 100:3 on a first electrode formed of indium tin oxide (ITO), thereby forming a first layer having a thickness of 100 Å. The compound represented by Formula 12 was deposited to have a thickness of 300 Å on the first layer, thereby forming a second layer.

The compound according to Example 4 of the present invention as a light-emitting host compound and the compound represented by Formula 14 as a light-emitting dopant compound were co-deposited at a weight ratio of 100:5 on the second layer, thereby forming a light-emitting layer having a thickness of about 200 Å.

And then, the compound represented by Formula 16 and Liq represented by Formula 15 were co-deposited at a weight ratio of 50:50 on the light-emitting layer, thereby forming an electron transporting layer having a thickness of about 360 Å. Subsequently, an electron injecting layer having a thickness of about 5 Å was formed on the electron transporting layer by using Liq represented by Formula 15.

A second electrode using an aluminum thin film having a thickness of 1,000 Å was formed on the electron injecting layer.

Blue Light-Emitting Device D-1 including the compound according to Example 4 of the present invention was manufactured by the above method.

Further, Light-Emitting Devices D-2 to D-7 were manufactured through a process which is substantially the same as the process of manufacturing Light-Emitting Device D-1, except that as the host compound of the light-emitting layer, each of the compounds according to Examples 5 to 10 of the present invention was used.

Manufacture of Comparative Devices 11 to 16

Comparative Devices 11 to 16 were manufactured through a process which is substantially the same as the process of manufacturing Light-Emitting Device D-1, except that as the host compound of the light-emitting layer, each of the compounds according to Comparative Examples 3 to 8 was used.

Evaluation of Power Efficiency and Lifespan of Light-Emitting Device

For each of Light-Emitting Devices D-1 to D-7 and Comparative Devices 11 to 16, an experiment, which is substantially the same as the experiment in which the power efficiency, lifespan, and color coordinate of Light-Emitting Devices A-1 to A-3 and Comparative Devices 1 and 2 were evaluated, was performed. The results are shown in Table 9.

TABLE 9

| Device No. | Power efficiency [lm/W] | Lifespan ($T_{50}$ [hr]) | Color coordinate (X, Y) |
| --- | --- | --- | --- |
| Light-Emitting Device D-1 | 7.4 | 258 | 0.146, 0.155 |
| Light-Emitting Device D-2 | 8.1 | 285 | 0.145, 0.154 |
| Light-Emitting Device D-3 | 7.2 | 237 | 0.144, 0.155 |
| Light-Emitting Device D-4 | 7.7 | 271 | 0.145, 0.155 |
| Light-Emitting Device D-5 | 7.9 | 279 | 0.147, 0.155 |
| Light-Emitting Device D-6 | 7.6 | 268 | 0.146, 0.156 |
| Light-Emitting Device D-7 | 7.1 | 229 | 0.144, 0.155 |
| Comparative Device 11 | 5.4 | 163 | 0.159, 0.162 |
| Comparative Device 12 | 5.2 | 157 | 0.158, 0.163 |
| Comparative Device 13 | 3.8 | 109 | 0.157, 0.161 |
| Comparative Device 14 | 5.1 | 152 | 0.157, 0.162 |
| Comparative Device 15 | 4.2 | 124 | 0.156, 0.162 |
| Comparative Device 16 | 4.6 | 139 | 0.158, 0.162 |

Referring to Table 9, it can be seen that the power efficiencies of Light-Emitting Devices D-1 to D-7 are 7.4 lm/W, 8.1 lm/W, 7.2 lm/W, 7.7 lm/W, 7.9 lm/W, 7.6 lm/W, and 7.1 lm/W, respectively, and the average power efficiency thereof is about 7.6 lm/W. In contrast, it can be seen that the power efficiencies of Comparative Devices 11 to 16 are 5.4 lm/W, 5.2 lm/W, 3.8 lm/W, 5.1 lm/W, 4.2 lm/W, and 4.6 lm/W, respectively, and the average power efficiency thereof is about 4.7 lm/W. Accordingly, it can be seen that the power efficiencies of Light-Emitting Devices D-1 to D-7 including the compound according to the present invention as a host compound of the light-emitting layer are significantly better than those of Comparative Devices 11 to 16. In particular, it can be seen that the power efficiency of Light-Emitting Device D-2 is improved by about 50% compared to that of Comparative Device 11.

In addition, it can be seen that the lifespans of Light-Emitting Devices D-1 to D7 are 258 hours, 285 hours, 237 hours, 271 hours, 279 hours, 268 hours, and 229 hours, respectively, and the average device lifespan thereof is about 261 hours. In contrast, it can be seen that the lifespans of Comparative Devices 11 to 16 are 163 hours or less, and the lifespan of Comparative Device 13 is only 109 hours. Accordingly, it can be seen that the lifespans of Light-Emitting Devices D-1 to D-7 including the compound according to the present invention as a host compound of the light-emitting layer are longer than those of Comparative Devices 11 to 16. In particular, it can be seen that the lifespan of Light-Emitting Device D-2 is increased by about 75% compared to that of Comparative Device 11.

Furthermore, referring to the color coordinate based on CIE 1931, it can be seen that when the compounds according to Examples 4 to 10 of the present invention are applied to the light-emitting layer of the blue light-emitting device as a host compound, the blue light-emitting device has little variation in the color coordinate while having improved power efficiency and increased lifespan.

Manufacture of Light-Emitting Devices E-1 to E-7

The compound represented by Formula 12 and the compound (HAT-CN) represented by Formula 11 were co-deposited at a weight ratio of 100:3 on a first electrode formed of indium tin oxide (ITO), thereby forming a first layer having a thickness of 100 Å. The compound represented by Formula 12 was deposited to have a thickness of 300 Å on the first layer, thereby forming a second layer.

A compound represented by the following Formula 17 was deposited on the second layer, thereby forming a blocking layer having a thickness of about 100 Å.

The compound according to Example 4 of the present invention as a light-emitting host compound and the compound represented by Formula 14 as a light-emitting dopant were co-deposited at a weight ratio of 100:5 on the blocking layer, thereby forming a light-emitting layer having a thickness of about 200 Å.

And then, the compound represented by Formula 16 and Liq represented by Formula 15 were co-deposited at a weight ratio of 50:50 on the light-emitting layer, thereby forming an electron transporting layer having a thickness of about 360 Å. Subsequently, an electron injecting layer having a thickness of about 5 Å was formed on the electron transporting layer by using Liq represented by Formula 15.

A second electrode using an aluminum thin film having a thickness of 1,000 Å was formed on the electron injecting layer.

[Formula 17]

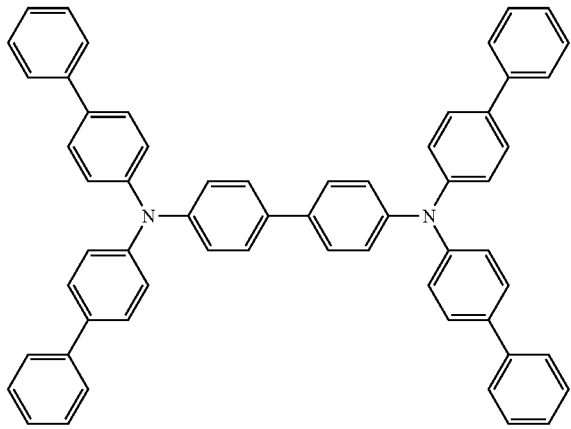

Blue Light-Emitting Device E-1 including the compound according to Example 4 of the present invention was manufactured by the above method.

Further, Light-Emitting Devices E-2 to E-7 were manufactured through a process which is substantially the same as the process of manufacturing Light-Emitting Device E-1, except that the host compound of the light-emitting layer was formed by using each of the compounds according to Examples 5 to 10 of the present invention.

Manufacture of Comparative Devices 17 to 22

Comparative Devices 17 to 22 were manufactured through a process which is substantially the same as the process of manufacturing Light-Emitting Device E-1, except that the light-emitting layer was formed by using each of the compounds according to Comparative Examples 3 to 8 as the host material of the light-emitting layer.

Evaluation of Power Efficiency and Lifespan of Light-Emitting Device

For each of Light-Emitting Devices E-1 to E-7 and Comparative Devices 17 to 22, an experiment, which is substantially the same as the experiment in which the power efficiency, lifespan, and color coordinate of Light-Emitting Devices A-1 to A-3 and Comparative Devices 1 and 2 were evaluated, was performed. The results are shown in Table 10.

TABLE 10

| Device No. | Power efficiency [lm/W] | Lifespan ($T_{50}$ [hr]) | Color coordinate (X, Y) |
|---|---|---|---|
| Light-Emitting Device E-1 | 7.9 | 287 | 0.146, 0.158 |
| Light-Emitting Device E-2 | 8.5 | 310 | 0.147, 0.156 |
| Light-Emitting Device E-3 | 7.4 | 265 | 0.145, 0.156 |
| Light-Emitting Device E-4 | 8.1 | 302 | 0.147, 0.155 |
| Light-Emitting Device E-5 | 8.3 | 305 | 0.148, 0.156 |
| Light-Emitting Device E-6 | 8.0 | 299 | 0.148, 0.155 |
| Light-Emitting Device E-7 | 7.6 | 272 | 0.146, 0.156 |
| Comparative Device 17 | 5.8 | 178 | 0.159, 0.163 |
| Comparative Device 18 | 5.6 | 172 | 0.159, 0.162 |
| Comparative Device 19 | 4.0 | 121 | 0.156, 0.163 |
| Comparative Device 20 | 5.4 | 167 | 0.158, 0.163 |
| Comparative Device 21 | 4.7 | 143 | 0.156, 0.163 |
| Comparative Device 22 | 5.1 | 160 | 0.159, 0.162 |

Referring to Table 10, it can be seen that the power efficiencies of Light-Emitting Devices E-1 to E-7 are 7.9 lm/W, 8.5 lm/W, 7.4 lm/W, 8.1 lm/W, 8.3 lm/W, 8.0 lm/W, and 7.6 lm/W, respectively, and the average power efficiency thereof is about 8.0 lm/W. In contrast, it can be seen that the power efficiencies of Comparative Devices 17 to 22 are 5.8 lm/W, 5.6 lm/W, 4.0 lm/W, 5.4 lm/W, 4.7 lm/W, and 5.1 lm/W, respectively, and the average power efficiency thereof is about 5.1 lm/W. Accordingly, it can be seen that the power efficiencies of Light-Emitting Devices E-1 to E-5 in which the compound according to the present invention is included in the light-emitting layer are significantly improved compared to those of Comparative Devices 17 to 22. In particular, it can be seen that the power efficiency of Light-Emitting Device E-2 is improved by about 47% compared to that of Comparative Device 17.

Further, it can be seen that the lifespans of Light-Emitting Devices E-1 to E-7 are 287 hours, 310 hours, 265 hours, 302 hours, 305 hours, 299 hours, and 272 hours, respectively, and the average lifespan thereof is about 291 hours, whereas the lifespans of Comparative Devices 17 to 22 are 178 hours, 172 hours, 121 hours, 167 hours, 143 hours, and 160 hours, respectively, and the average lifespan thereof is about 157 hours. Accordingly, it can be seen that the lifespans of Light-Emitting Devices E-1 to E-5 in which the compound according to the present invention is included in the light-emitting layer are increased compared to those of Comparative Devices 17 to 22. In particular, it can be seen that the lifespan of Light-Emitting Device E-2 is increased by about 74% compared to that of Comparative Device 17.

Meanwhile, referring to the color coordinate based on CIE 1931, it can be seen that when the compounds according to Examples 4 to 10 of the present invention are applied to the light-emitting layer of the blue light-emitting device as a host compound, the blue light-emitting device has little variation in the color coordinate while having improved power efficiency and increased lifespan.

| EXPLANATION OF CODES | |
|---|---|
| 100, 102, 104: Light-emitting device | 10: Base substrate |
| 20: First electrode | 30, 32, 34: Hole transport layer |
| 40: Light-emitting layer | 50: Second electrode |
| 60: Electron transporting layer | |

What is claimed is:
1. A compound selected from the group consisting of the following Structures 1 to 9:
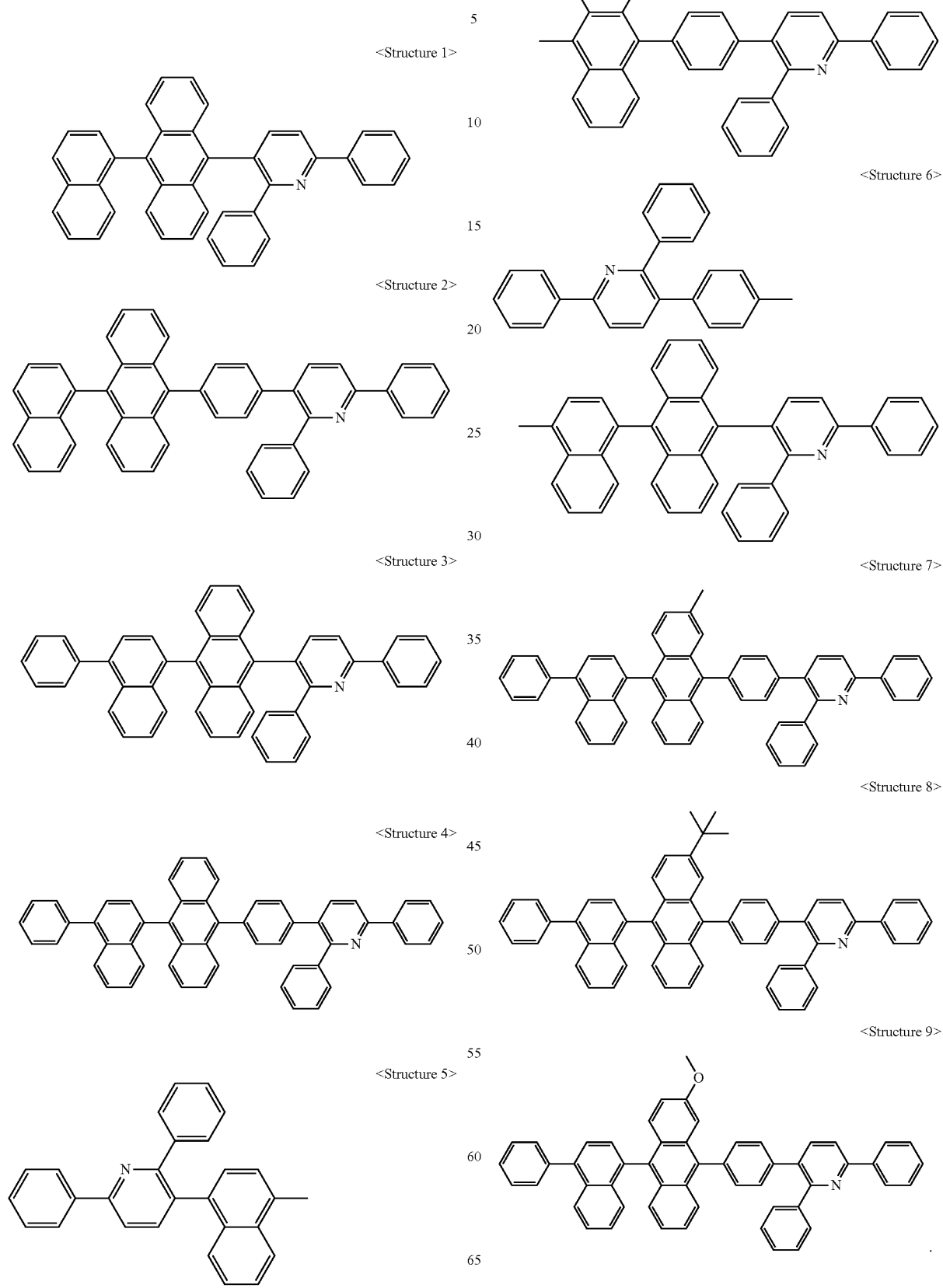

2. A compound represented by the following Formula 3-1:

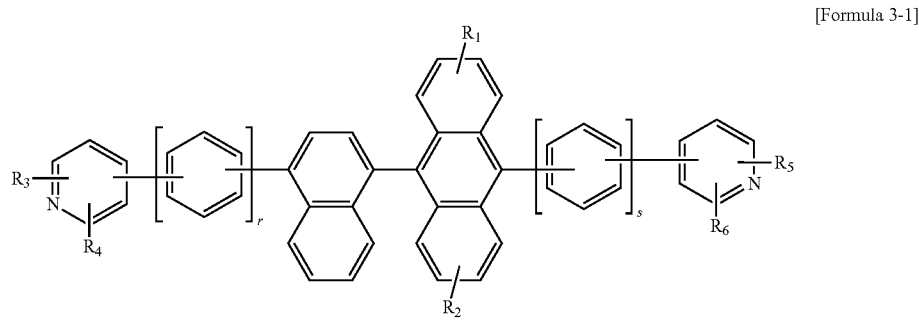

[Formula 3-1]

in Formula 3-1,
$R_1$ and $R_2$ each independently represent hydrogen, an alkyl group having 1 to 30 carbon atoms, or an alkoxy group having 1 to 30 carbon atoms,
r and s each identically represent 0 or 1, and
$R_3$, $R_4$, $R_5$, and $R_6$ represent a phenyl group.

3. The compound of claim 2, wherein the compound represented by Formula 3-1 is selected from the following Structures 1 and 2:

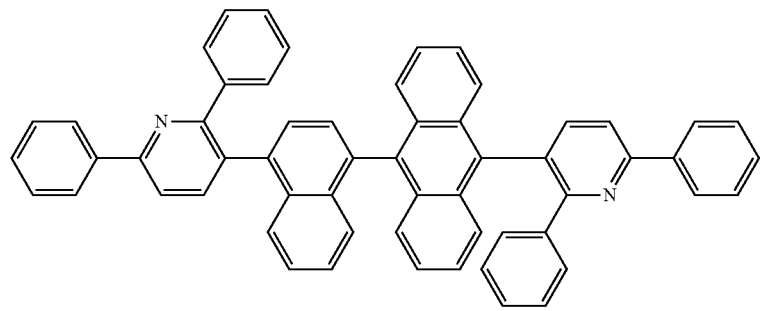

<Structure 1>

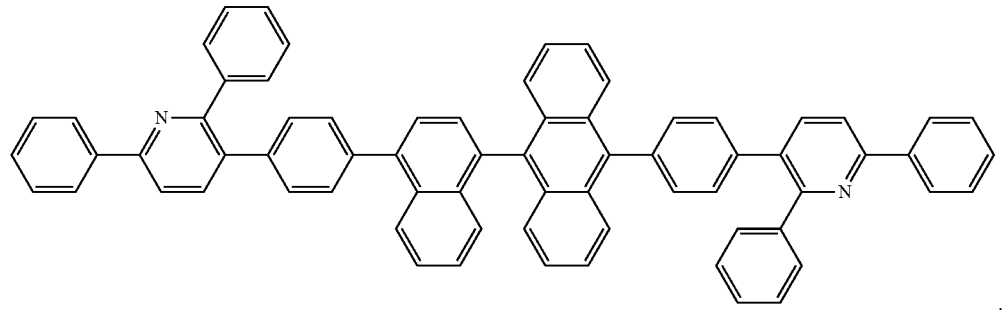

<Structure 2>

4. A compound represented by the following Formula 4:

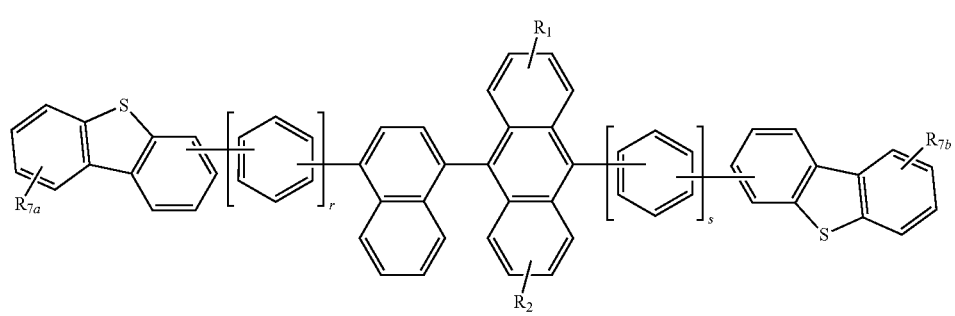

[Formula 4]

in Formula 4, $R_1$ and $R_2$ each independently represent hydrogen, an alkyl group having 1 to 30 carbon atoms, or an alkoxy group having 1 to 30 carbon atoms, r and s each independently represent 0 or 1, and $R_{7a}$ and $R_{7b}$ each independently represent hydrogen, or an alkyl group having 1 to 30 carbon atoms.

5. The compound of claim 4, wherein the compound represented by Formula 4 is selected from the following Structures 1 to 10:

<Structure 1>

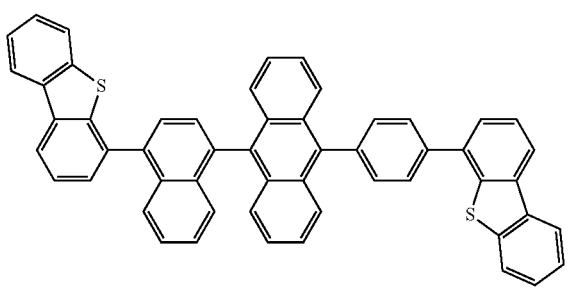

-continued

<Structure 3>

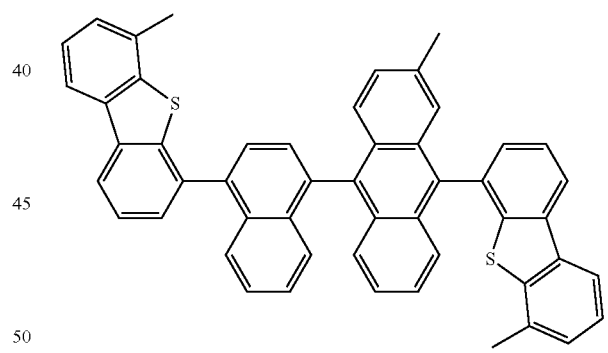

<Structure 4>

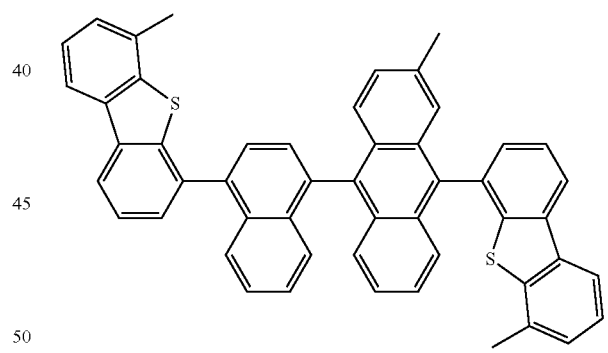

<Structure 2>

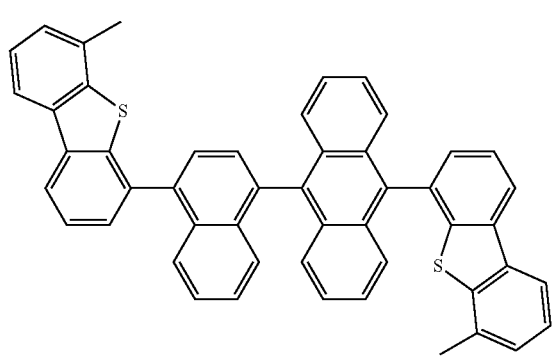

<Structure 5>

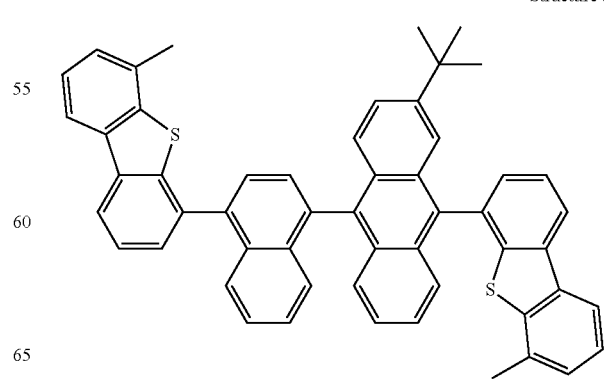

-continued
<Structure 6>
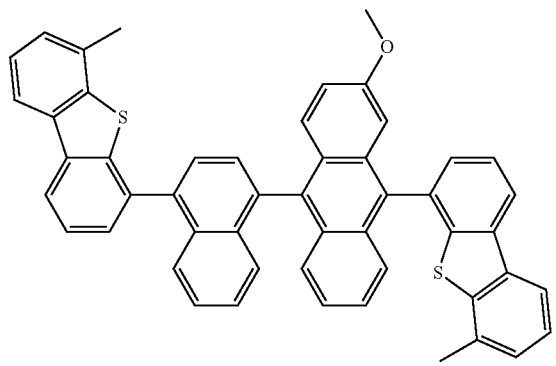
<Structure 7>
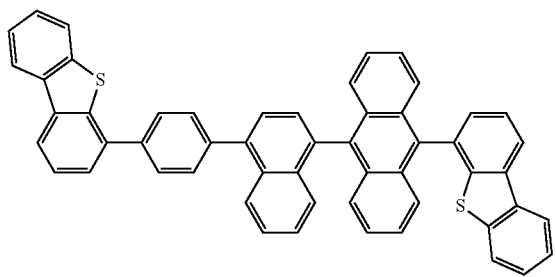
<Structure 8>
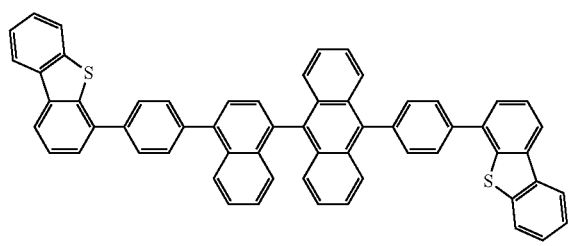
-continued
<Structure 9>
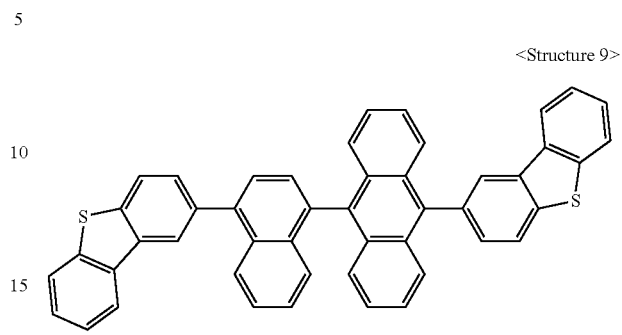
<Structure 10>
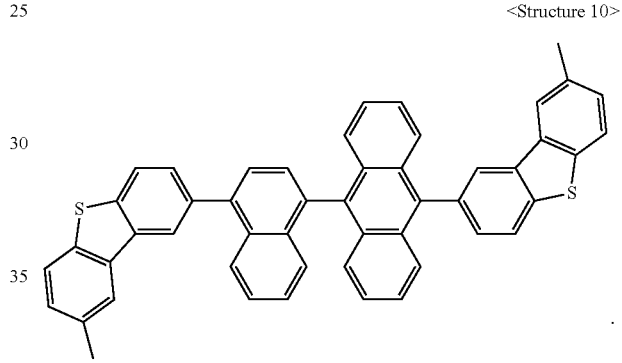
6. A compound represented by the following Formula 5:
[Formula 5]
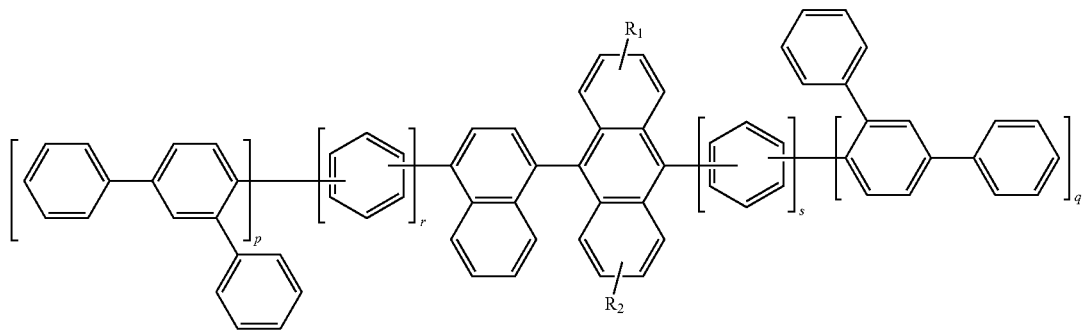

in Formula 5,

R₁ and R₂ each independently represent hydrogen, an alkyl group having 1 to 30 carbon atoms, or an alkoxy group having 1 to 30 carbon atoms, p and q each independently represent 0 or 1, in which p+q=1 or 2, and r and s each independently represent an integer of 0 to 2.

7. The compound of claim 6, wherein the compound represented by Formula 5 is selected from the following Structures 1 to 9:

<Structure 1>

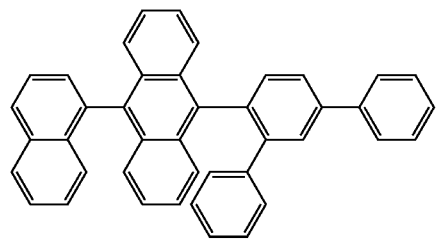

<Structure 2>

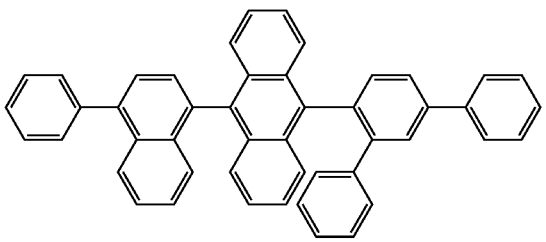

<Structure 3>

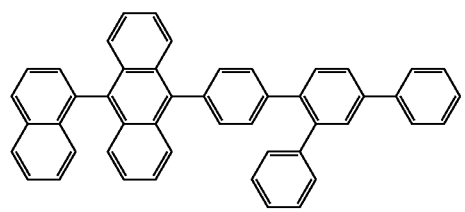

<Structure 4>

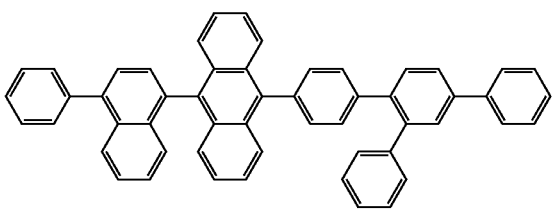

<Structure 5>

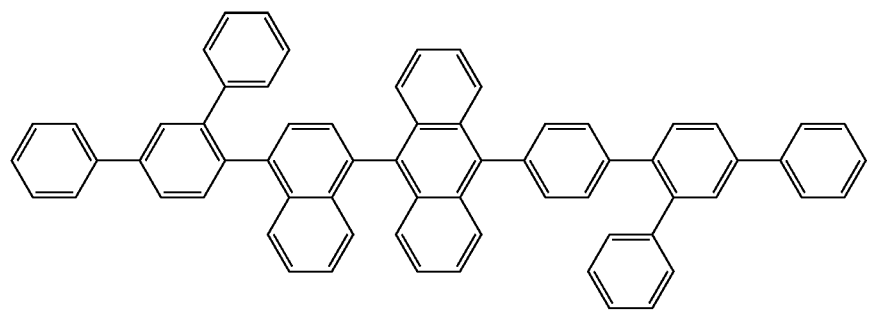

<Structure 6>

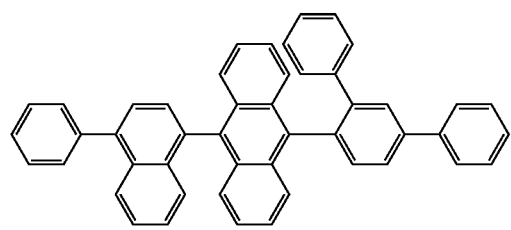

<Structure 7>

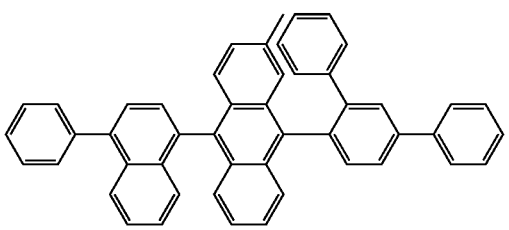

<Structure 8>

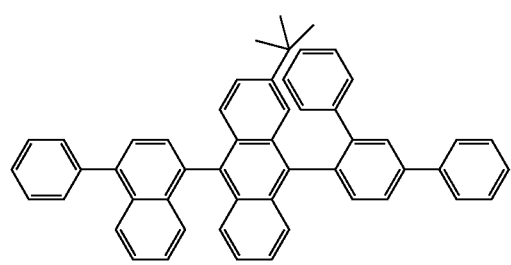

<Structure 9>

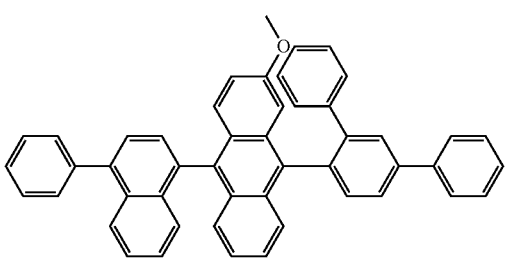

8. The compound of claim 6, wherein the compound represented by Formula 5 is represented by the following Formula 5-1:

[Formula 5-1]

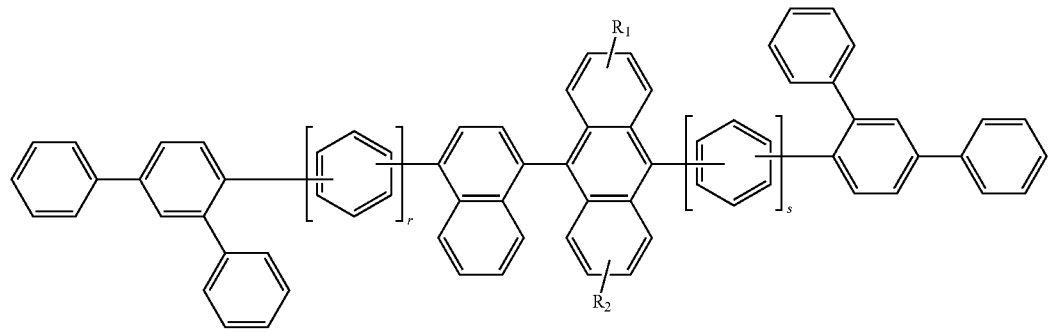

in Formula 5-1,
R₁ and R₂ each independently represent hydrogen, an alkyl group having 1 to 30 carbon atoms, or an alkoxy group having 1 to 30 carbon atoms, and
r and s each identically represent an integer of 0 to 2.

9. The compound of claim 8, wherein the compound represented by Formula 5-1 is selected from the following Structures 1 and 2:

<Structure 1>

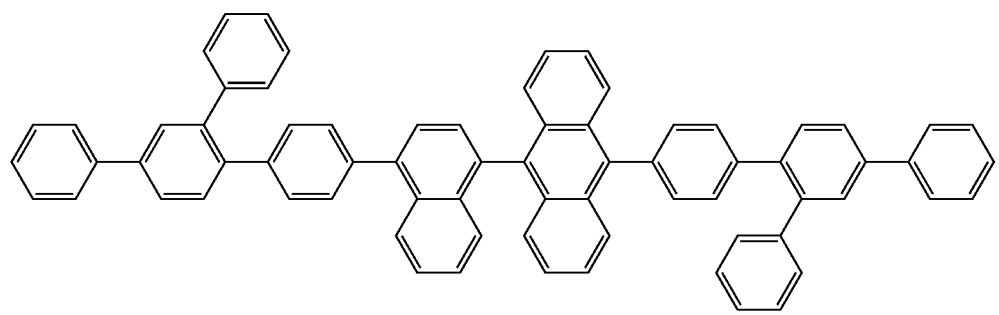

<Structure 2>

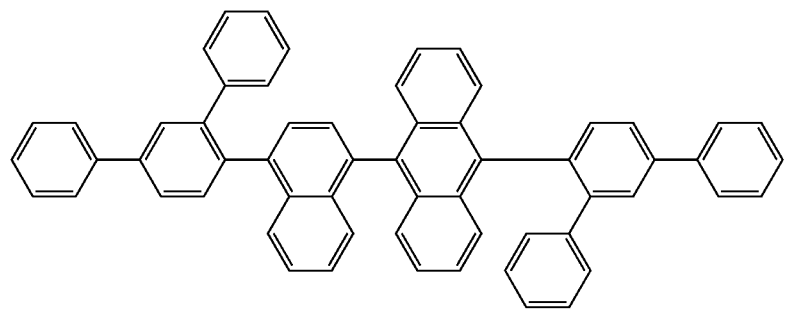

10. A light-emitting device comprising:
a first electrode;
a second electrode; and
an organic layer disposed between the first electrode and the second electrode and comprising the compound of claim 1.

11. A light-emitting device comprising:
a first electrode;
a second electrode; and
an organic layer disposed between the first electrode and the second electrode and comprising the compound of claim 2.

12. A light-emitting device comprising:
a first electrode;
a second electrode,
an organic layer disposed between the first electrode and the second electrode and comprising the compound of claim 4.

13. A light-emitting device comprising:
a first electrode;
a second electrode; and
an organic layer disposed between the first electrode and the second electrode and comprising the compound of claim 6.

* * * * *